Figure 1:
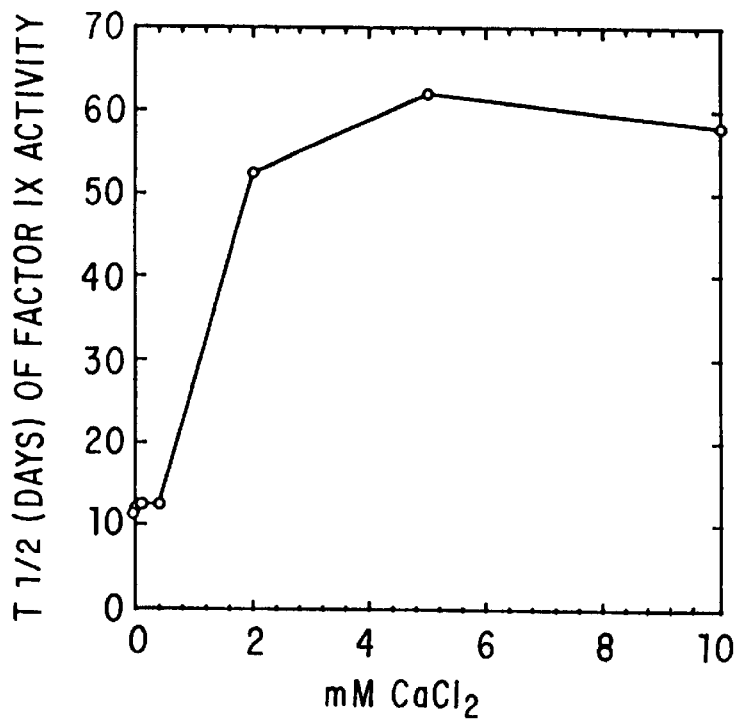

United States Patent [19]

Miekka et al.

[11] Patent Number: 5,925,738
[45] Date of Patent: Jul. 20, 1999

[54] METHODS OF PRODUCTION AND USE OF LIQUID FORMULATIONS OF PLASMA PROTEINS

[75] Inventors: Shirley I. Miekka, Gaithersburg, Md.; William N. Drohan, Springfield, Va.; Thomas R. Jameson; Manish P. Singh, both of Gaithersburg, Md.; John R. Taylor, Jr., New York, N.Y.; Martin J. MacPhee, Montgomery Village, Md.

[73] Assignees: The American National Red Cross, Washington, D.C.; The Coalition for Hemophilia B, New York, N.Y.

[21] Appl. No.: 08/758,560

[22] Filed: Nov. 29, 1996

Related U.S. Application Data

[60] Provisional application No. 60/007,866, Dec. 1, 1995.

[51] Int. Cl.⁶ .................................................. A61K 35/14
[52] U.S. Cl. ......................... 530/380; 530/383; 530/384; 530/829; 530/830; 514/21
[58] Field of Search ..................................... 530/380, 383, 530/384, 829, 830; 514/21

[56] References Cited

U.S. PATENT DOCUMENTS

| | | | |
|---|---|---|---|
| 3,560,475 | 2/1971 | Fekete et al. | 530/380 |
| 4,447,416 | 5/1984 | Memadre-Aronson et al. | 530/380 |
| 5,055,557 | 10/1991 | Zimmermann | 530/381 |
| 5,110,907 | 5/1992 | Kosow et al. | 530/383 |
| 5,259,951 | 11/1993 | Arrigli et al. | 210/660 |
| 5,288,853 | 2/1994 | Bhattacharva et al. | 530/383 |
| 5,639,857 | 6/1997 | Zimmermann | 530/384 |

*Primary Examiner*—Cecilia J. Tsang
*Assistant Examiner*—Abdel A-Mohamed
*Attorney, Agent, or Firm*—Sterne, Kessler, Goldstein & Fox P.L.L.C.

[57] ABSTRACT

The present invention relates to the preparation and use of liquid formulations of plasma proteins, particularly blood coagulation factors. More specifically, the present invention relates to stable liquid formulations of Factor VIII and Factor IX that can be administered by injection or infusion to provide a constant level of the coagulation factor in the blood.

22 Claims, 31 Drawing Sheets

| LANE | SAMPLE |
|------|--------|
| 1 | BMW STD. |
| 2 | EMPTY |
| 3 | 10 mM Ca, pH 5.8 |
| 4 | 10 mM Ca, pH 6.0 |
| 5 | 10 mM Ca, pH 6.2 |
| 6 | 30 mM Ca, pH 5.8 |
| 7 | 30 mM Ca, pH 6.0 |
| 8 | 30 mM Ca, pH 6.2 |
| 9 | 100 mM Ca, pH 5.8 |
| 10 | 100 mM Ca, pH 6.0 |
| 11 | 100 mM Ca, pH 6.2 |

DAY 0, NON-REDUCED

| LANE | SAMPLE |
|------|--------|
| 1 | BMW STD. |
| 2 | EMPTY |
| 3 | 10 mM Ca, pH 5.8 |
| 4 | 10 mM Ca, pH 6.0 |
| 5 | 10 mM Ca, pH 6.2 |
| 6 | 30 mM Ca, pH 5.8 |
| 7 | 30 mM Ca, pH 6.0 |
| 8 | 30 mM Ca, pH 6.2 |
| 9 | 100 mM Ca, pH 5.8 |
| 10 | 100 mM Ca, pH 6.0 |
| 11 | 100 mM Ca, pH 6.2 |

DAY 56, NON-REDUCED pH 5.8 pH 6.0 pH 6.2 pH 5.8 pH 6.0 pH 5.8 pH 6.0

METHODS OF PRODUCTION AND USE OF LIQUID FORMULATIONS OF PLASMA PROTEINS

This application claims the benefit of the filing date of provisional application Ser. No. 60/007,866, filed Dec. 1, 1995.

I. FIELD OF THE INVENTION

The present invention relates to the preparation and use of liquid formulations of plasma proteins, particularly blood coagulation factors. More specifically, the present invention relates to stable liquid formulations of Factor VIII and Factor IX and to the treatment of congenital or acquired deficiencies of plasma proteins by continuous injection or infusion of these formulations to provide a constant level of the coagulation factor in the blood.

II. BACKGROUND OF THE INVENTION

A. COAGULATION

Coagulation of blood occurs by either the "intrinsic pathway" or the "extrinsic pathway", whereby certain blood proteins interact in a cascade of proteolytic activations to ultimately convert soluble fibrinogen to insoluble fibrin. These threads of fibrin are cross-linked to form the scaffolding of a clot; without fibrin formation, coagulation cannot occur.

The intrinsic pathway consists of seven steps: (1) the proteolytic activation of Factor XII; (2) activated Factor XII cleaves Factor XI to activate it; (3) activated Factor XI cleaves Factor IX, thereby activating it; (4) activated Factor IX interacts with activated Factor VIII to cleave and activate Factor X; (5) activated Factor X binds to activated Factor V on a membrane surface, which complex proteolytically cleaves prothrombin to form thrombin; (6) thrombin proteolytically cleaves fibrinogen to form fibrin; (7) fibrin monomers assemble into fibrils, which are then cross-linked by Factor XIII.

The extrinsic pathway consists of the following steps: (1) upon rupture of a blood vessel, Factor VII binds to tissue factor, a lipoprotein present in tissues outside the vascular system; (2) Factor VII is activated to Factor VIIa by proteolytic cleavage; and (3) the Factor VIIa-tissue factor complex cleaves and activates Factor X. Thereafter, the extrinsic pathway is identical to the intrinsic pathway, i.e. the two pathways share the last three steps described above.

One of the plasma proteins, coagulation Factor IX ("CFIX") is synthesized in the liver by hepatocytes as a 415 amino-acid polypeptide and then post-translationally modified to a glycoprotein of molecular weight 56,000 Daltons by a carboxylase requiring vitamin K as a cofactor. CFIX is thus one of the group of "vitamin K-dependent" plasma proteins.

Factor VII is another vitamin K-dependent clotting protein that is similar to CFIX in size and structure.

Factor VIII, a non-vitamin K-dependent protein, is a much larger protein, with a molecular wieght of near 300,000 daltons (300 kDa). It is activated by thrombin, which cleaves the molecule in several places to form Factor VIIIa (the activated form). In plasma, Factor VIII binds to von Willebrand Factor (vWF) and circulates as complexes with vWF, which stabilizes the labile Factor VIII molecule.

Disturbing the balance of the cascade involved in the intrinsic pathway results in various coagulation disorders. The absence or reduction of an intrinsic Factor X-activating moiety (a "tenase") at step (4) results in the defective-coagulation condition known as hemophilia. Hemophilia A, the most common, results from a mutation in the gene for Factor VIII; Hemophilia B, also known as Christmas Disease, results from a mutation in the gene for Factor IX. Hemophilia B, like Hemophilia A, is X-linked and accounts for approximately 12% of hemophilia cases. The symptoms are identical to those of Hemophilia A: excessive bleeding upon injury; and spontaneous bleeding, especially into weight-bearing joints, soft tissues, and mucous membranes. Repeated bleeding into joints results in hemarthroses, causing painful crippling arthropathy that often necessitates joint replacement. Hematomas in soft tissues can result in pseudo tumors composed of necrotic coagulated blood; they can obstruct, compress, or rupture into adjacent organs and can lead to infection. Once formed the hematomas are difficult to treat, even with surgery. Recovery of nerves after compression is poor, resulting in palsy. Those bleeding episodes that involve the gastrointestinal tract, central nervous system, or airway/retroperitoneal space can lead to death if not detected. Intracranial bleeding is a major cause of death in hemophiliacs.

Current treatment of these symptoms consists of intravenous replacement therapy with Factor VIII or Factor IX concentrates. Treatment of major bleeding episodes is by bolus injection of concentrate. As described above, however, tissue damage remains even after prompt detection and treatment. Prophylactic treatment is recommended to prevent this pain and debilitation. Upon injection, 50% of Factor IX is immediately bound to vascular endothelial cells and/or diffuses into the extravascular space. The remaining 50% has a half life in circulation of approximately 24 hours. These infusion kinetics result in the need for injections once to twice per week or more to maintain minimal therapeutic levels in the plasma. While this regimen is inconvenient and stressful for the patient, it is also not totally effective. Progressive, cumulative tissue damage continues with each bleeding episode prior to the onset of treatment.

B. VITAMIN K-DEPENDENT PLASMA PROTEINS

The group that comprises the vitamin K-dependent plasma proteins consists to date of Factor II, Factor VII, Factor IX, Factor X, Protein C, Protein S, and Protein Z. These proteins exhibit significant homology on all levels: gene organization, amino acid sequence (primary structure), protein folding (secondary structure), post-translational modifications, activation, and function (Hedner and Davie, Chapter 84: Introduction to Hemostasis and the Vitamin K-Dependent Coagulation Factors, in C. R. Scriver et al. (Eds.), *Metabolic Basis of Inherited Disease*, 6th edition, McGraw-Hill, New York N.Y., (1989), pp. 2107–2134). A comparison of the features of the six- well-characterized vitamin K-dependent plasma proteins follows (Protein Z is excluded due to a paucity of information regarding its properties and function):

| Feature | Factor II | Factor VII | Factor IX | Factor X | Protein C | Protein S |
|---|---|---|---|---|---|---|
| No. gla domains | 10 | 10 | 12 | 11 | 9 | 11 |
| No. EGF's (w/β) | 2 Kringle | 2 | 2 | 2 | 2 | 4 β's |
| Activation cleavage | 2 by Xa | 1 by Xa | 2 by XIa | 2 by IXa | 1 by IIa | — |
| Function | serine protease | serine protease | serine protease | serine protease | serine protease | cofactor, Protein C |
| Catalytic domain | His43 Asp99 Ser205 | His41 Asp90 Ser192 | His41 Asp89 Ser185 | His42 Asp88 Ser185 | His42 Asp88 Ser191 | — |
| No. carbohydrates | 3 | 3 | 2 | 2 | 4 | 3 |

The "gla" domains consist of the first 40 to 45 amino acid residues with multiple γ-carboxyglutamic acid residues that are formed by the carboxylation of the amino acid glutamic acid by a membrane-bound complex requiring vitamin K. They are required for the calcium-dependent binding of the protein to phospholipid surfaces.

The "EGF" domains are composed of 40 to 50 amino acids that show considerable sequence similarity to Epidermal Growth Factor (EGF) and its precursor. The first EGF domain in each of these proteins contains a β-hydroxyaspartic acid modification. While Protein S does not contain these EGF domains, it does contain three β-hydroxyaspartic acid residues and one β-hydroxyasparagine residue. Factor II, also known as prothrombin, contains 2 Kringle regions in the place of these EGF domains. These Kringle domains are also found in Factor XII, Plasminogen, Tissue Plasminogen Activator, and Urokinase, which while not vitamin K-dependent proteins, are plasma proteins with proteolytic activity that are involved in coagulation.

Five of the six vitamin K-dependent plasma proteins are activated by proteolytic cleavage by the preceding member of the coagulation cascade. Three have two cleavages, releasing an activation peptide that shielded the catalytic domain. Activation of Factor X by Factor IXa involves a single cleavage that releases an activation peptide from the heavy chain of this two-chain protein. Factor VII is activated by a single cleavage of the single chain of the polypeptide, without the release of an activation peptide.

Five of the six vitamin K-dependent plasma proteins are serine proteases upon activation. These proteases have histidine, aspartic acid, and serine residues in analogous positions within their catalytic domains. Protein S is a cofactor for Protein C and does not in itself have a catalytic domain known at this time.

The six vitamin K-dependent plasma proteins are glycoproteins with two to four N-linked glycosylation sites in the EGF and catalytic domains and/or activation peptides.

The vitamin K-dependent plasma proteins are similar enough in characteristics to co-purify throughout most of their purification procedures. All six vitamin K-dependent plasma proteins are found in the same fractions throughout most steps of both commonly used purification procedures. The barium citrate or aluminum hydroxide adsorptions of Cohn fractions co-purify Factors II, VII, IX, and X as well as Protein C; anion exchange chromatography on resins such as DEAE-Sephadex or DEAE-Sepharose co-purifies Factors II, IX, and X along with trace amounts of Factor VII and Protein C, from cryo-poor plasma.

C. CURRENT FACTOR IX PREPARATIONS

The two manufacturers that have Factor IX concentrates on the U.S. market provide them in lyophilized form. Armour Pharmaceuticals (now Centeon) produces Mononine, which, upon reconstitution with sterile water for injection (WFI), is delivered in a composition of: 0.01 moles/liter histidine, pH 7.05; 0.066 moles/liter sodium chloride; 3% mannitol. AlphaNine SD is manufactured by Alpha Therapeutics and upon reconstitution with sterile WFI is delivered in a composition that includes: 0.04 units heparin/unit FIX; 1 milligram dextrose/unit FIX. One lot of Mononine was found to have an in vitro half life when reconstituted of 13 days at 37° C. To avoid repeated invasive treatments as is found with the current therapies for prophylaxis, stabilities of at least 30 days at 37° C. and at least 365 days at 4° C. are necessary.

D. CURRENT FACTOR VIII PREPARATIONS

Three manufacturers produce affinity-purified plasma Factor VIII concentrates for the U.S. market, all of which are lyophillized products. Baxter Healthcare/Hyland Division manufactures two products by the same method: Antihemophilic Factor (Human), Method M, Monoclonal Purified (AHF-M) is produced for the American Red Cross (ARC) from volunteer donor plasma collected by the ARC; and Hemophil M is produced from commercial plasmapheresis plasma. These products, upon reconstitution with sterile WFI, are delivered in a composition of 12.5 mg/mL human albumin, 1.5 mg/mL PEG, 0.030 M glycine, and 0.055 M histidine. Armour/Centeon produces Monoclate, which upon reconstitution with sterile WFI is delivered in a composition of 10–20 mg/mL human albumin, 0.30–0.45 M sodium chloride, 2–5 mM calcium chloride, 0.8% mannitol and 1.2 mM histidine. Alphanate, manufactured by Alpha Therapeutic Corporation, upon reconstitution with sterile WFI is delivered in a composition of 0.5–10 mg/mL human albumin and not more than 10 mM calcium, 2 μ/mL heparing, 0.055 M histidine and 0.3 M arginine.

In addition, two freeze-dried recombinant Factor VIII products are presently on the market. Recombinate is produced by Baxter HealthCare and Kogenate is produced by Bayer Corporation.

E. OTHER STABLE AQUEOUS PLASMA PROTEIN PREPARATIONS

The components of fibrin sealant, or fibrin glue, have been formulated in liquid that results in an activity half life of greater than 6 months at 4° C. for both the thrombin and fibrinogen concentrate components (Chabbat et al., Thrombos. Res. 76:525–533 (1994)). The thrombin component is in a formulation of: arginine, 1.6 millimoles/liter; benzamidine less than 1 milligram/liter; gluconate, 1.7 millimoles/liter; calcium, 22 millimoles/liter; pH 6.6. The fibrinogen concentrate component is in a formulation of: aprotinin, 250 Kiu/milliliter; glycine, 1.2 grams/liter; ethanol, less than 0.1 grams/liter; pH 7.6.

F. NON-AQUEOUS LIQUID PROTEIN FORMULATIONS

There are very few precedents for the formulation of pharmaceutically significant proteins in non-aqueous liquid formulations. However, the components of Fibrin Sealant, fibrinogen and thrombin (activated Factor II), have been formulated in a non-aqueous ethanol solution to facilitate storage and delivery of these components in a single delivery unit without premature activation.

G. DELIVERY OF PHARMACEUTICAL PREPARATIONS BY CONTINUOUS INFUSION

Pumps have been in use for the continuous delivery of pharmaceuticals in liquid formulation. External syringe-delivery pumps are used in the U.S. and abroad for the delivery of insulin, antibiotics, chemotherapeutics, and hormones. These pumps can deliver liquids in programmed continuous doses or in bolus injections, as necessary, for intravenous, subcutaneous, or intraperitoneal delivery. Reservoir capacity ranges from 1 milliliter to 1500 milliliters. The pumps are powered by batteries with a 2 to 3 month life. It is therefore desirable for the liquid Factor IX formulation to have a stability of at least 30 days at 37° C., requiring physician oversight once per month instead of twice per week as for the current prophylactic therapy. Externally worn pumps of the types described have been used to deliver Factor VIII and Factor IX to hemophilia patients for short-term perisurgical prophylaxis to prevent excessive bleeding that could otherwise occur with invasive procedures.

In addition, two implantable pumps are available for use in humans, but have not been employed for delivering coagulation factors to hemophilia patients. These pumps are designed to be surgically implanted in the chest wall or abdomen, cushioned by subcutaneous fat, with the exit catheter anchored for peritoneal, hepatic artery or perispinal access. The pumps are filled externally by injection through the skin. The Arrow Model 3000 Implantable Pump (Arrow Therix, Walpole, Mass.) is licensed for clinical use and is applied primarily for the delivery of pain medications and chemotherapeutic agents for liver cancer. It operates by a titanium bellows with a capacity of 30 mL and can be obtained in three pre-set flow rates: 0.5, 1.0 and 2.0 mL/day, with special hypodermic needles for bolus infusion. The MiniMed 2001 (MiniMed Technologies, Sylmar, Calif.) is awaiting licensure for use in delivery of insulin. This peristatic pump has a titanium reservoir with a capacity of 15–18 mL and can be externally controlled by a programmable communicator, allowing for variable flow rates and bolus override when required.

Hydrogels, particularly chitin hydrogels or chitosan hydrogels, have previously been used for sustained drug release (Chandy and Sharma, Biomat. *Art. Cells & Immob. Biotech.* 19:745–760 (1991)). More recently, in vivo release of Factor IX from a subcutaneous injection of a negatively charged derivative of chitosan, N,O-carboxymethyl chitosan (NOCC), that had Factor IX incorporated within it, demonstrated that slow diffusional release from the hydrogel resulted in the appearance of the Factor IX in the plasma and at lower peak levels that more closely approximated normal levels than did direct subcutaneous injection of Factor IX without the hydrogel; it also resulted in longer delivery of Factor IX at clinically significant levels (Oral presentation at *XVth Congress of the International Society on Thrombosis and Haemostasis*, Jerusalem, Israel on Jun. 11, 1995).

III. SUMMARY OF THE INVENTION

It is therefore an object of the present invention to provide stable liquid formulations of Factor VIII and Factor IX that can be administered to an individual to provide a constant circulating level of the coagulation factor. Other objects, features and advantages of the present invention will be set forth in the detailed description of preferred embodiments that follows, and in part will be apparent from the description or may be learned by practice of the invention. These objects and advantages of the invention will be realized and attained by the compositions and methods particularly pointed out in the written description and claims hereof.

The effectiveness of the liquid formulations of the present invention is determined by the inherent characteristics of the proteins themselves and the ability of the formulations of the present invention to retain those characteristics that determine biological activity.

In one embodiment, this invention provides a composition of matter, comprising a plasma protein in a stable liquid formulation.

In another embodiment, this invention provides a composition of matter whereby the plasma protein is a vitamin K-dependent plasma protein such as coagulation Factors II, VII, IX, X, Proteins C, S and Z, as either a proenzyme or in activated form.

In another embodiment, this invention provides a composition of matter whereby the plasma protein is a non-vitamin K-dependent plasma protein.

In another embodiment, this invention provides a composition of matter whereby the plasma protein is coagulation Factor VIII, von Willebrand Factor, or the like.

In another embodiment, this invention provides a composition of matter whereby the plasma protein is provided in an aqueous liquid formulation.

In another embodiment, this invention provides a composition of matter whereby the plasma protein is provided in a non-aqueous liquid formulation.

In another embodiment, this invention provides a composition of matter whereby the plasma protein is provided in a hydrophilic non-aqueous liquid formulation.

In another embodiment, this invention provides a composition of matter whereby the plasma protein is provided in a mixed aqueous/non-aqueous liquid formulation.

In another embodiment, this invention provides a composition of matter whereby the plasma protein is functionally stable at or near body temperature.

In another embodiment, this invention provides a composition of matter whereby the plasma protein is functionally stable at or near refrigeration temperature.

In another embodiment, this invention provides a composition of matter whereby the plasma protein is deliverable without prior rehydration.

In another embodiment, this invention provides a composition of matter whereby the plasma protein is deliverable by injection.

In another embodiment, this invention provides a composition of matter whereby the plasma protein is deliverable by a biologically-derived bio-resorbable hydrogel, such as a chitin hydrogel or a chitosan hydrogel.

In another embodiment, this invention provides a composition of matter whereby the plasma protein is deliverable intranasally.

In another embodiment, this invention provides a composition of matter whereby the plasma protein is deliverable by inhalation.

In another embodiment, this invention provides a composition of matter whereby the plasma protein is deliverable orally.

In another embodiment, this invention provides a method of treating congenital or acquired deficiencies of plasma proteins by delivery of the deficient plasma protein.

In another embodiment, this invention provides a method of treating deficiencies of plasma proteins whereby delivery of the deficient protein is by continuous injection or infusion.

In another embodiment, this invention provides a method of treating deficiencies of plasma proteins whereby the continuous delivery of the deficient protein is by diffusion from a biologically-derived bio-resorbable hydrogel, such as a chitosan hydrogel or NOC-chitosan hydrogel.

It is to be understood that both the foregoing general description and the following detailed description are exemplary and explanatory only and are intended to provide further explanation of the invention as claimed.

IV. BRIEF DESCRIPTION OF THE FIGURES

FIG. 1. Dependence of Factor IX Stability on $CaCl_2$ Concentration.

Aliquots of Factor IX-M at 100 units/mL in 0.01 M Histidine, 0.1 M NaCl, pH 6.8 with varied concentrations of $CaCl_2$ ranging from 0–10 mM, were incubated at 37° C. for time periods up to 50 days and assayed for Factor IX activity according to the method of Example 1. The half lives, in days, for each $CaCl_2$ concentration tested were plotted against that concentration. The stability rose quickly by 2 mM, peaked at 5 mM, and leveled through 10 mM $CaCl_2$.

Figure 2:
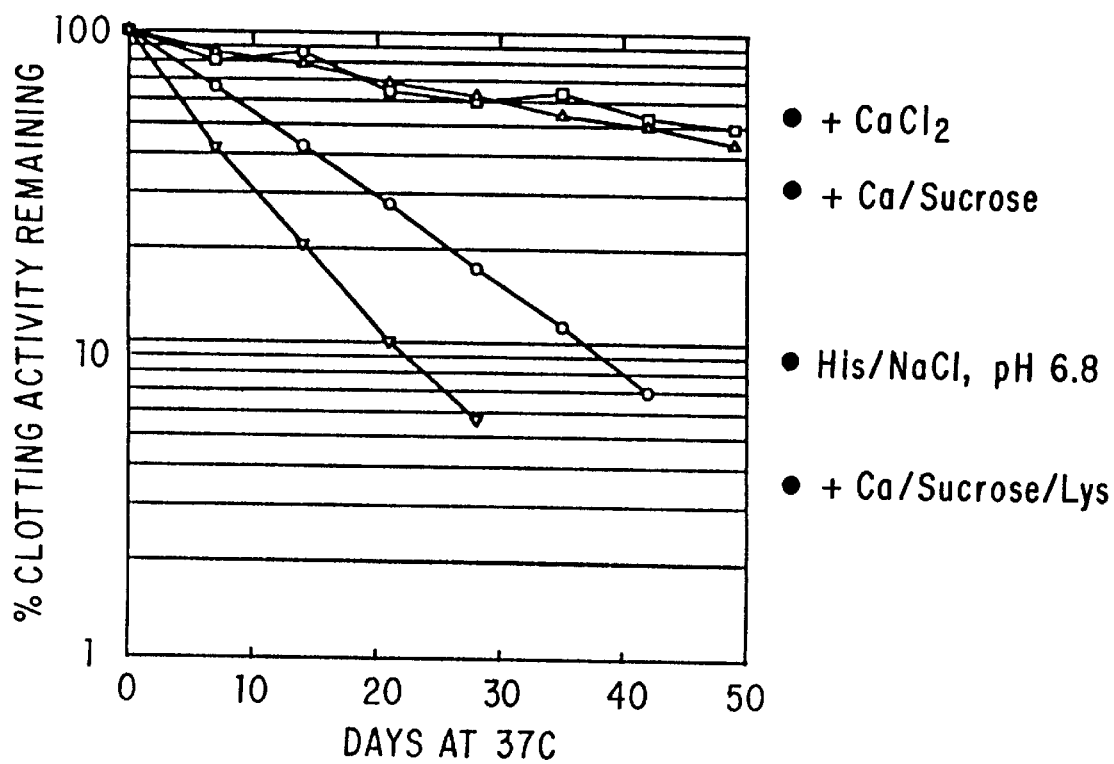

FIG. 2. Stability of Factor IX-M (100 units/mL) in Sterile Solutions at 37° C. Data summarized in Example 3 are graphed here. The addition of $CaCl_2$ greatly enhances the stability of Factor IX over the same buffer without calcium, while the addition of sucrose does not further enhance that stability. The formulation of Octapharma, which adds lysine to the calcium/sucrose formulation, significantly reduces the stability of Factor IX over those formulations without lysine.

Figure 3:
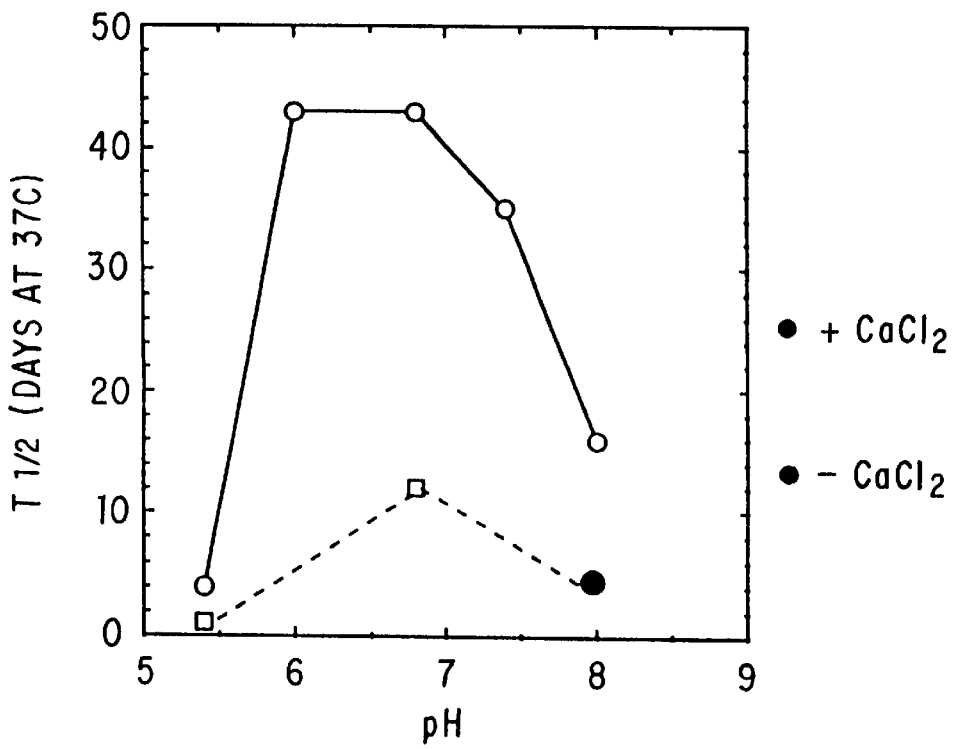

FIG. 3. pH Dependence of FIX-M Stability+/- 10 mM $CaCl_2$. Aliquots of Factor IX-M at 100 units/mL in 0.01 M Histidine, 0.1 M NaCl, with and without 10 mM $CaCl_2$, at varying pH, were incubated at 37° C. for 0–42 days and assayed for Factor IX activity according to the method of Example 1. The half lives, in days, were plotted against pH. The stability was much greater in the presence of calcium than in the absence for all pH. Within each calcium level, the stability was greater closer to neutral pH, with the greatest stability at pH 6.0–6.8 in the presence of calcium.

Figure 4:
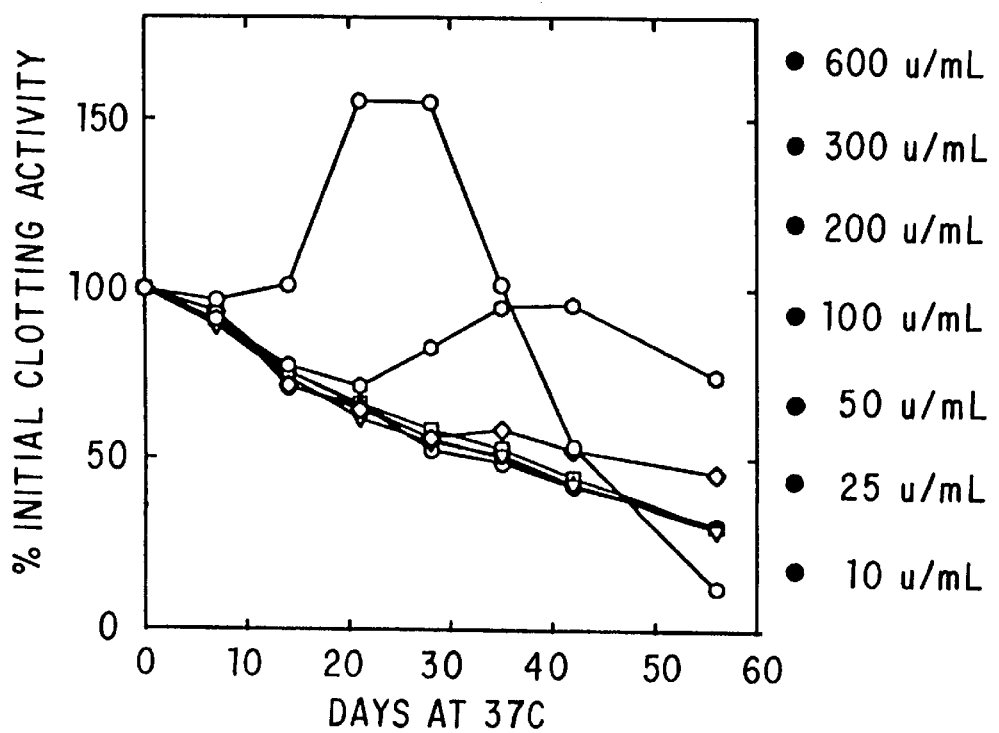

FIG. 4. Factor IX Shows Evidence of Activation When Incubated at High Concentrations. Aliquots of Factor IX-M in 0.01 M Histidine, 0.1 M NaCl, 10 mM $CaCl_2$, pH 6.8, was incubated at 37° C. at varying concentrations of Factor IX, ranging from 10 units(u)/mL to 600 u/mL. Percent of initial activity for each concentration was plotted against days at 37° C. Lower concentrations of Factor IX, from 10 u/mL through 100 u/mL, showed no effect of concentration on stability. As the concentration of Factor IX increased, the activity increased then fell, with the peak of activity occurring earlier for higher Factor IX concentrations. The indication is that at higher concentrations Factor IX exhibits activation, with a spike of activity followed by a decline as the Factor IX loses stability once activated.

Figure 5A:
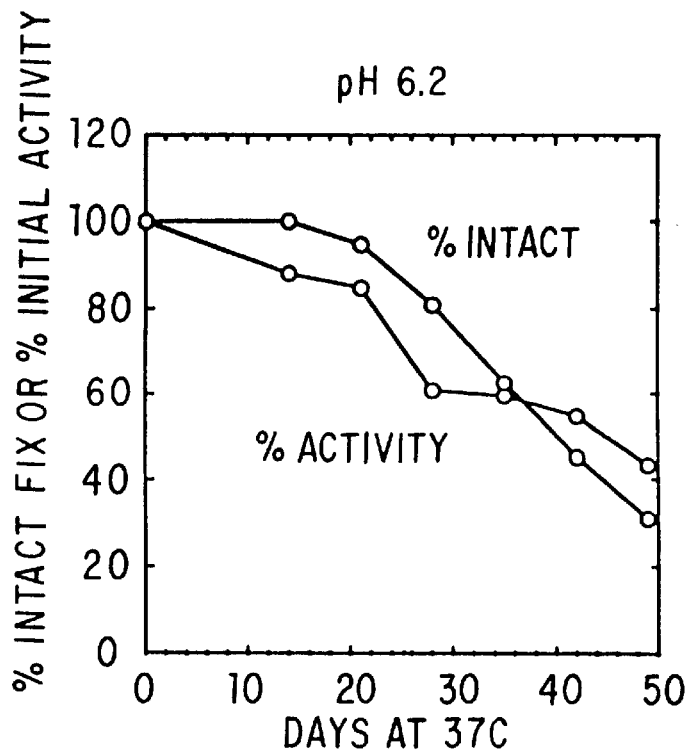
Figure 5B:
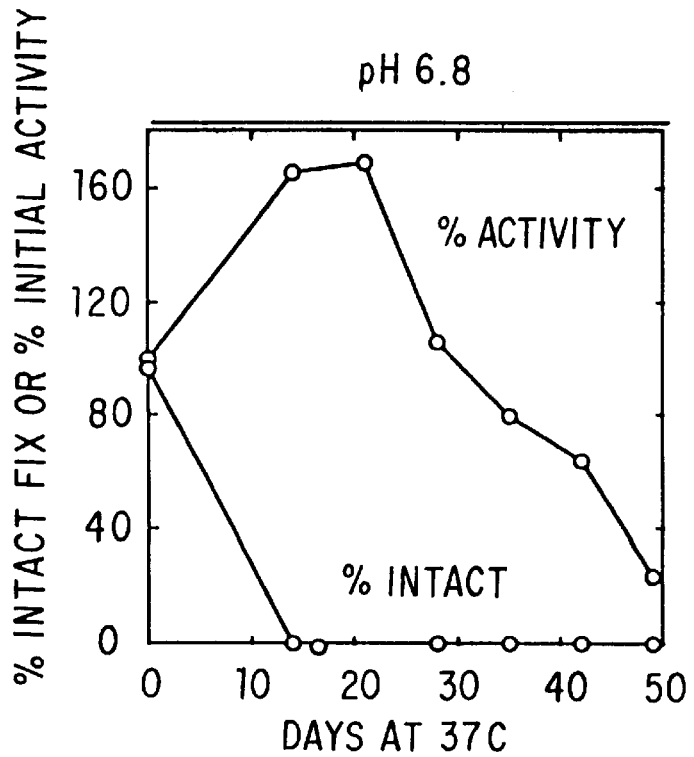

FIG. 5A, 5B. At High Concentrations, FIX-M Stability is Maximal at pH 6.0–6.2. Aliquots of FIX-M at 600 u/mL in 0.01 M Histidine, 0.1 M NaCl, 10 mM $CaCl_2$, at pH 6.0 or 6.8, were incubated at 37° C. for 0–50 days and assayed for Factor IX activity according to the method in Example 1. Percent of initial activity and percent intact FIX-M were plotted against days at 37° C. At pH 6.2, FIG. 5A, both the percent intact and the percent activity had half lives of 40–45 days. At pH 6.8, FIG. 5B, the percent activity spiked at 15–20 days and dropped with a half life of 40–45 days, but the percent intact dropped to zero at 14 days. At high Factor IX concentrations the higher pH destabilizes the protein while a lower pH enhances the stability.

Figure 6:
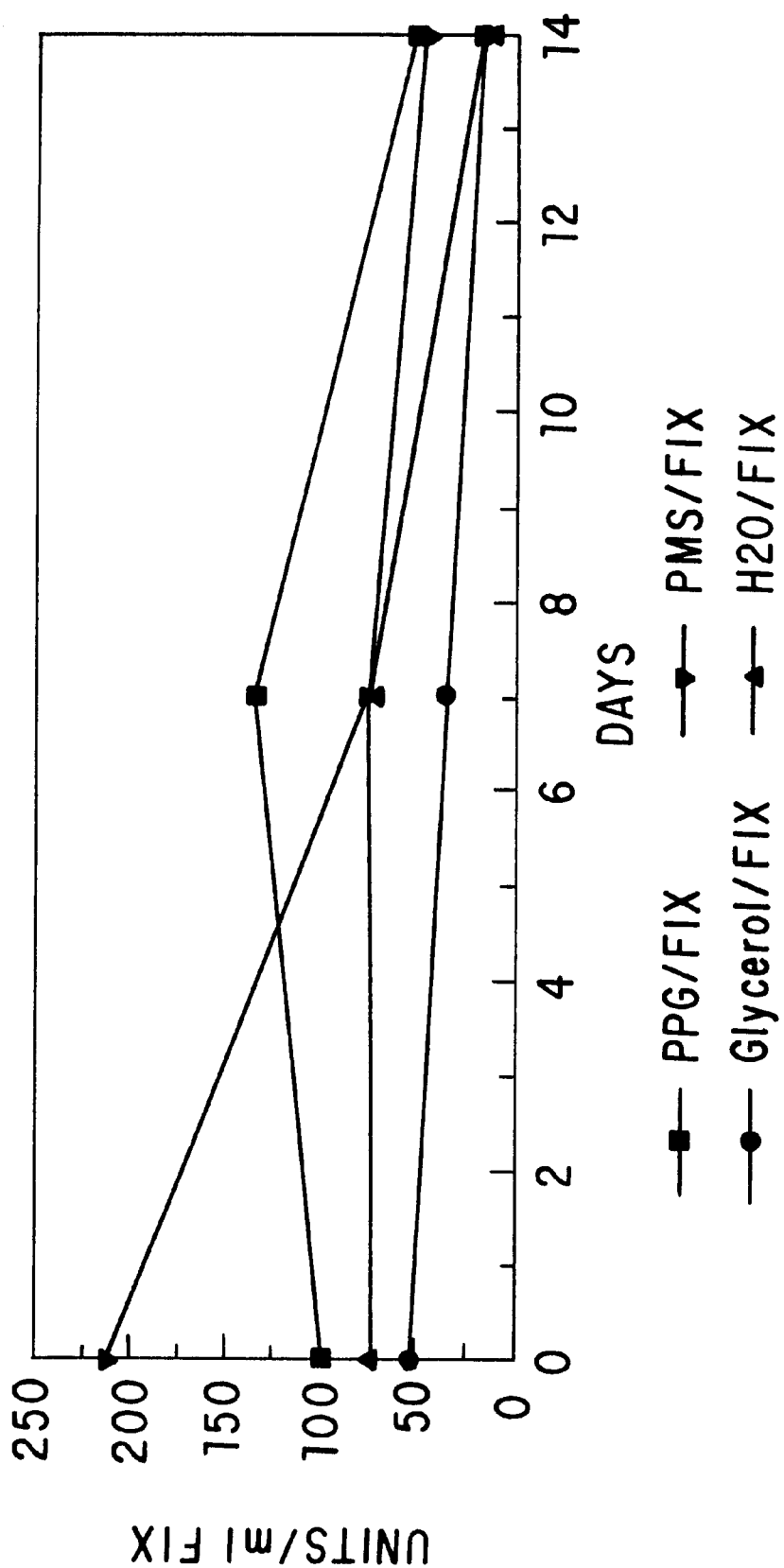

FIG. 6. FIX in PPG, Glycerol and PMS Formulations Incubated at 37° C. Data from Example 4 are graphed here. PPG provides the greatest stability, with a half life of 14 days at 37° C. The initial material reconstituted in water and in glycerol provided half lives two and three days shorter, respectively. PMS provided the least stability, with a half life of 5.5 days.

Figure 7:
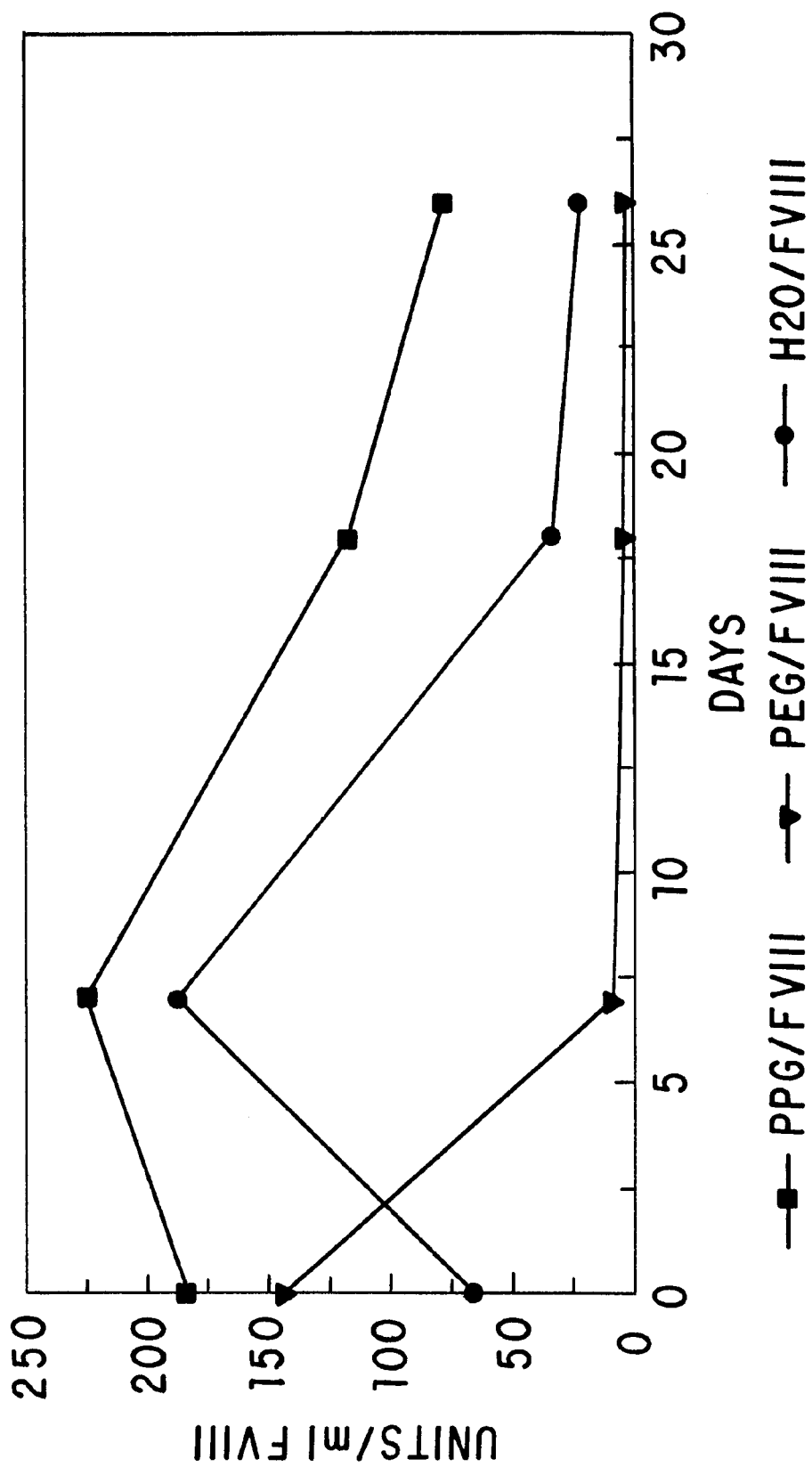

FIG. 7. FVIII PPG and PEG Formulations at 37° C. Data from Example 5 are graphed here. PPG, like for Factor IX, provides the greatest stability for Factor VIII. Reconstitution in water provides somewhat less stability and PEG greatly destabilizes the activity.

Figure 8:
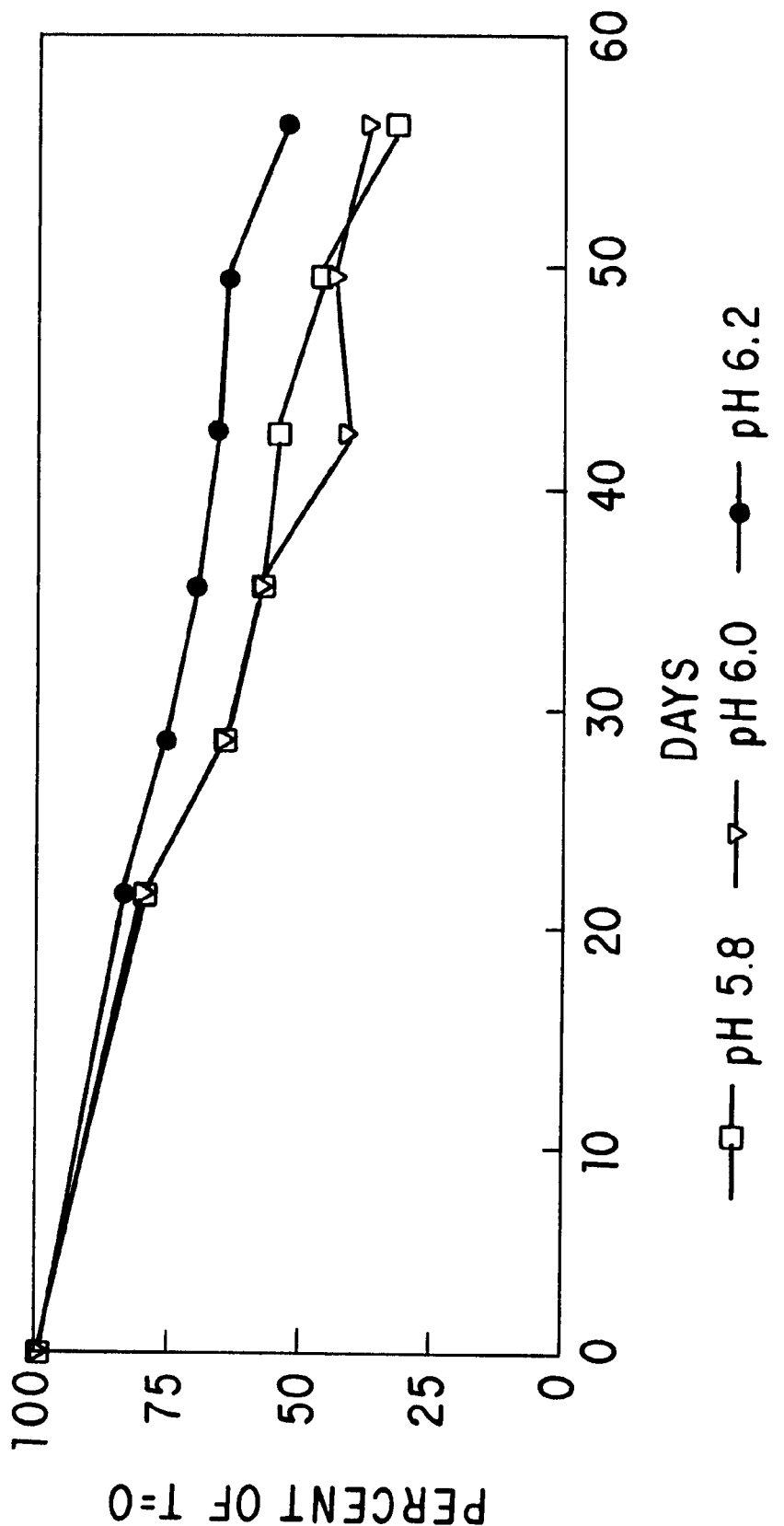

FIG. 8. FIX Stability with 10 mM $CaCl_2$ at 37° C. Data from Example 6 are graphed here. When the results at each of the three pH values tested were plotted, the half-life of clotting activity varied from 38 to 58 days, with a slightly biphasic curve suggestive of activation at pH 6.2. Stability was greatest in the range of pH 6.0–6.2.

Figure 9:
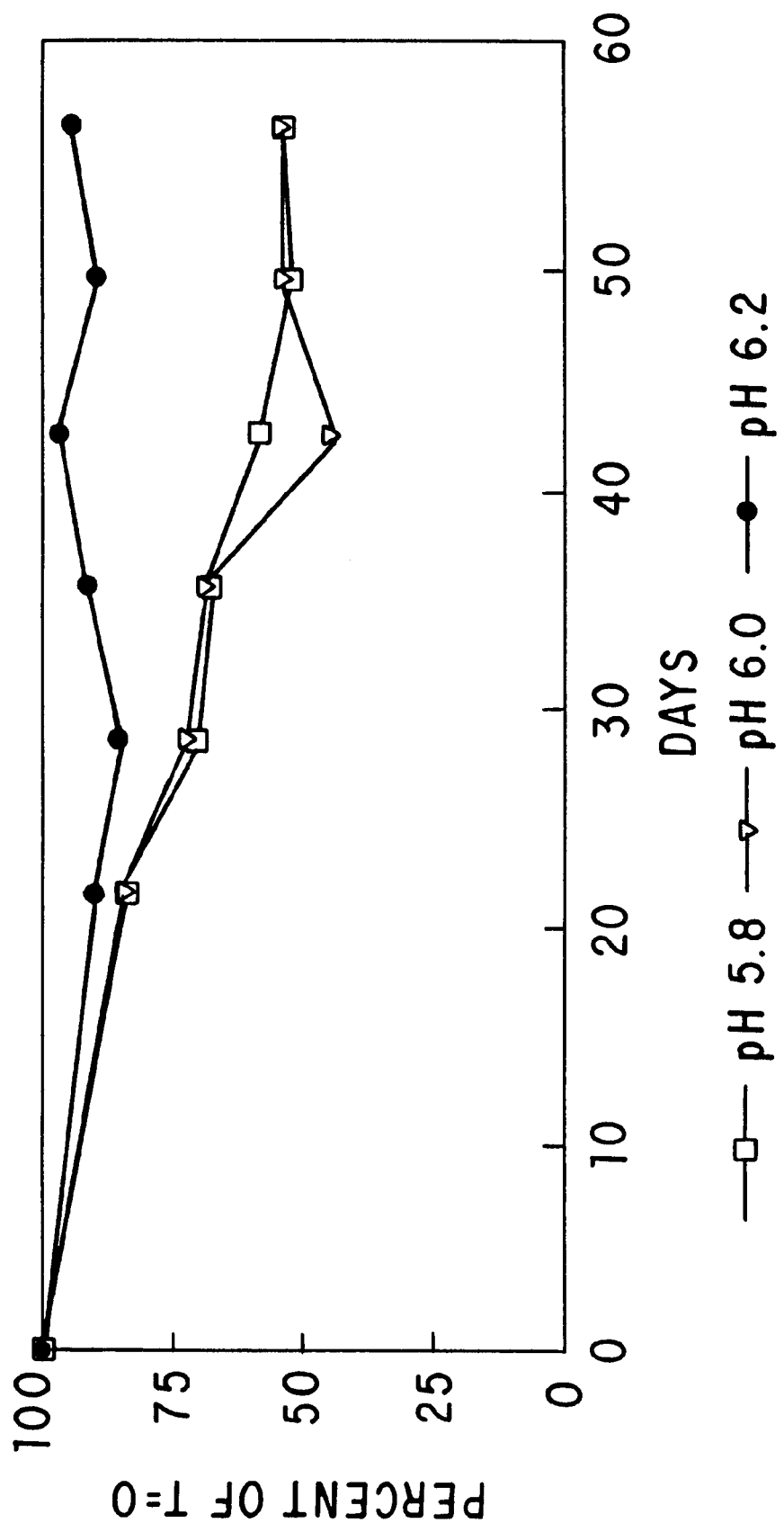

FIG. 9. FIX Stability with 30 mM $CaCl_2$ at 37° C. Data from Example 6 are graphed here. When the results at each of the three pH values tested were plotted, evidence of activation at pH 6.2 was observed. Stability was greatest in the range of pH 5.8–6.2.

Figure 10:
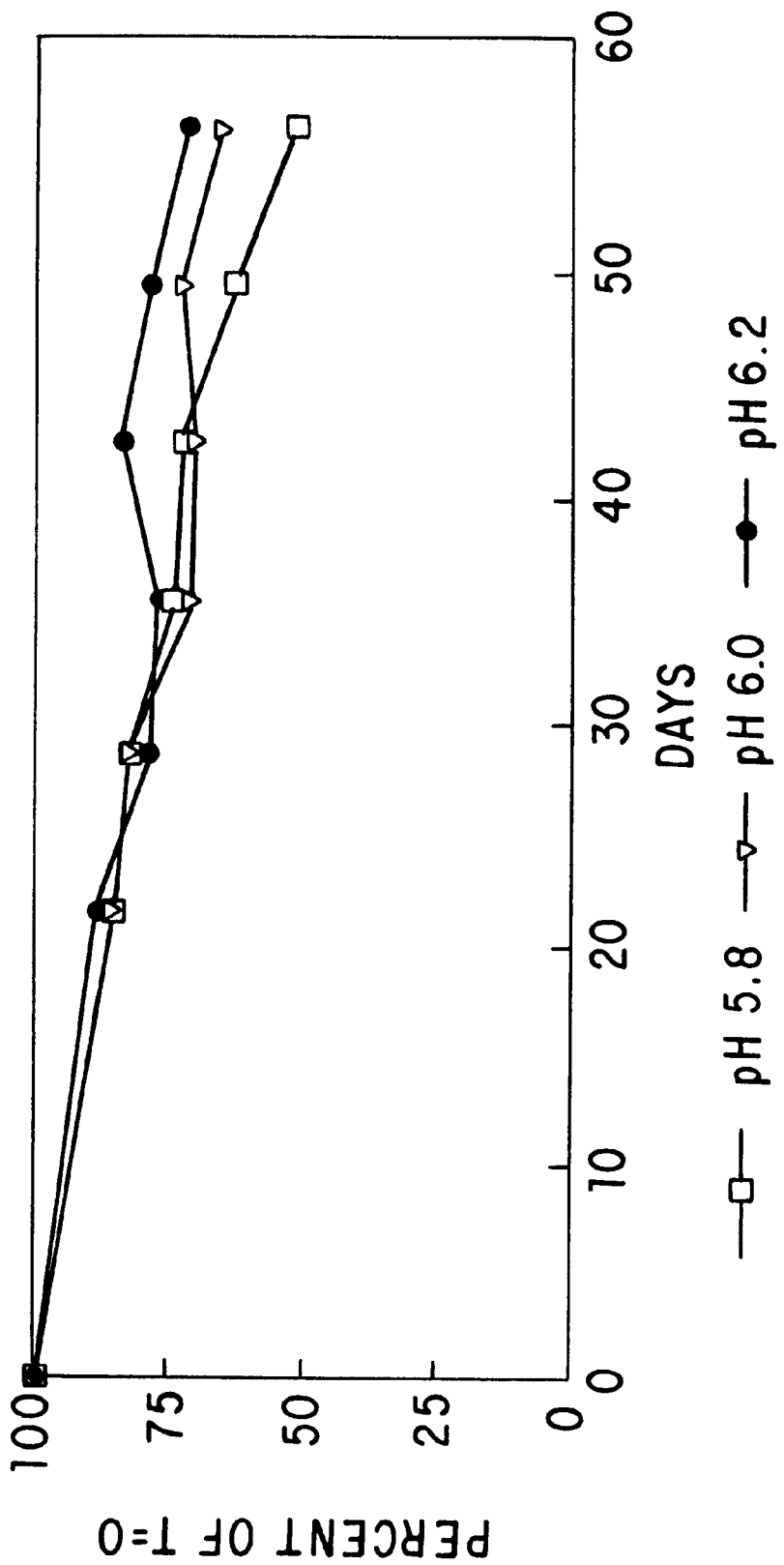

FIG. 10. FIX Stability with 100 mM $CaCl_2$ at 37° C. Data from Example 6 are graphed here. When the results at each of the three pH values tested were plotted, a slight indication of activation is observed after 40 days at pH 6.0 and pH 6.2. Stability was greatest at pH 5.8.

Figure 11:
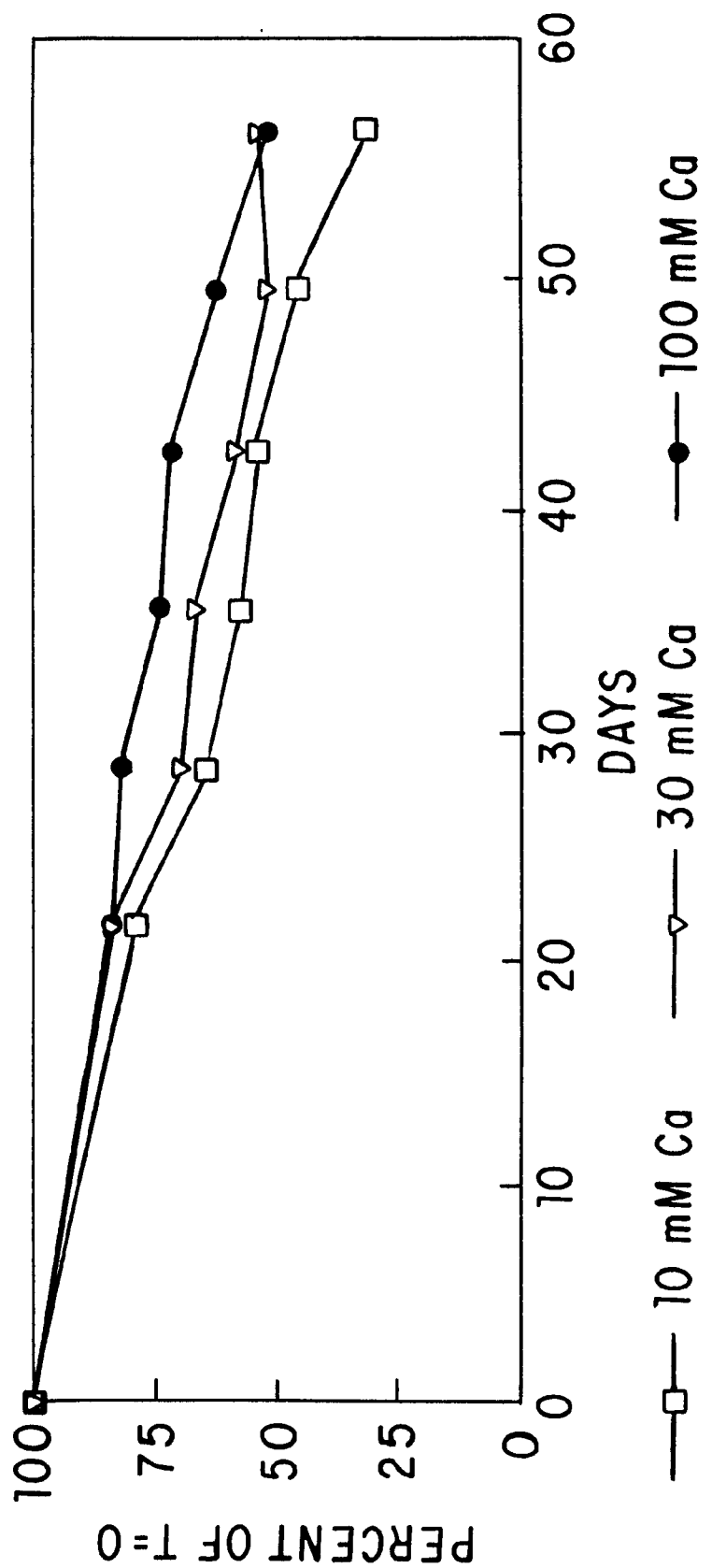

FIG. 11. FIX Stability at pH 5.8 with varying concentrations of $CaCl_2$ at 37° C. Data from Example 6 are graphed here.

Figure 12:
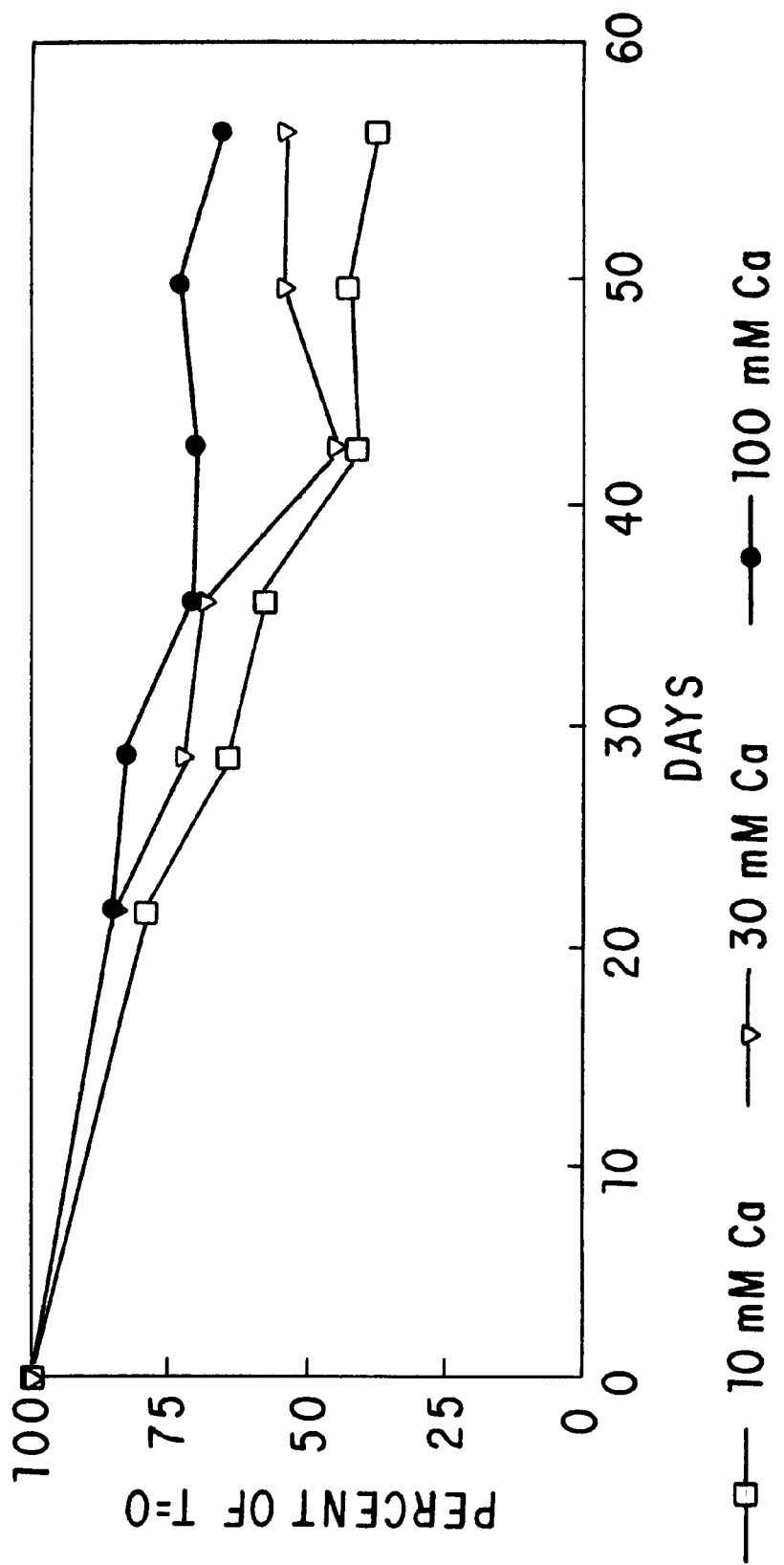

FIG. 12. FIX Stability at pH 6.0 with varying concentrations of $CaCl_2$ at 37° C. Data from Example 6 are graphed here. The shallower decay curve observed with 100 mM $CaCl_2$ may reflect activation.

Figure 13:
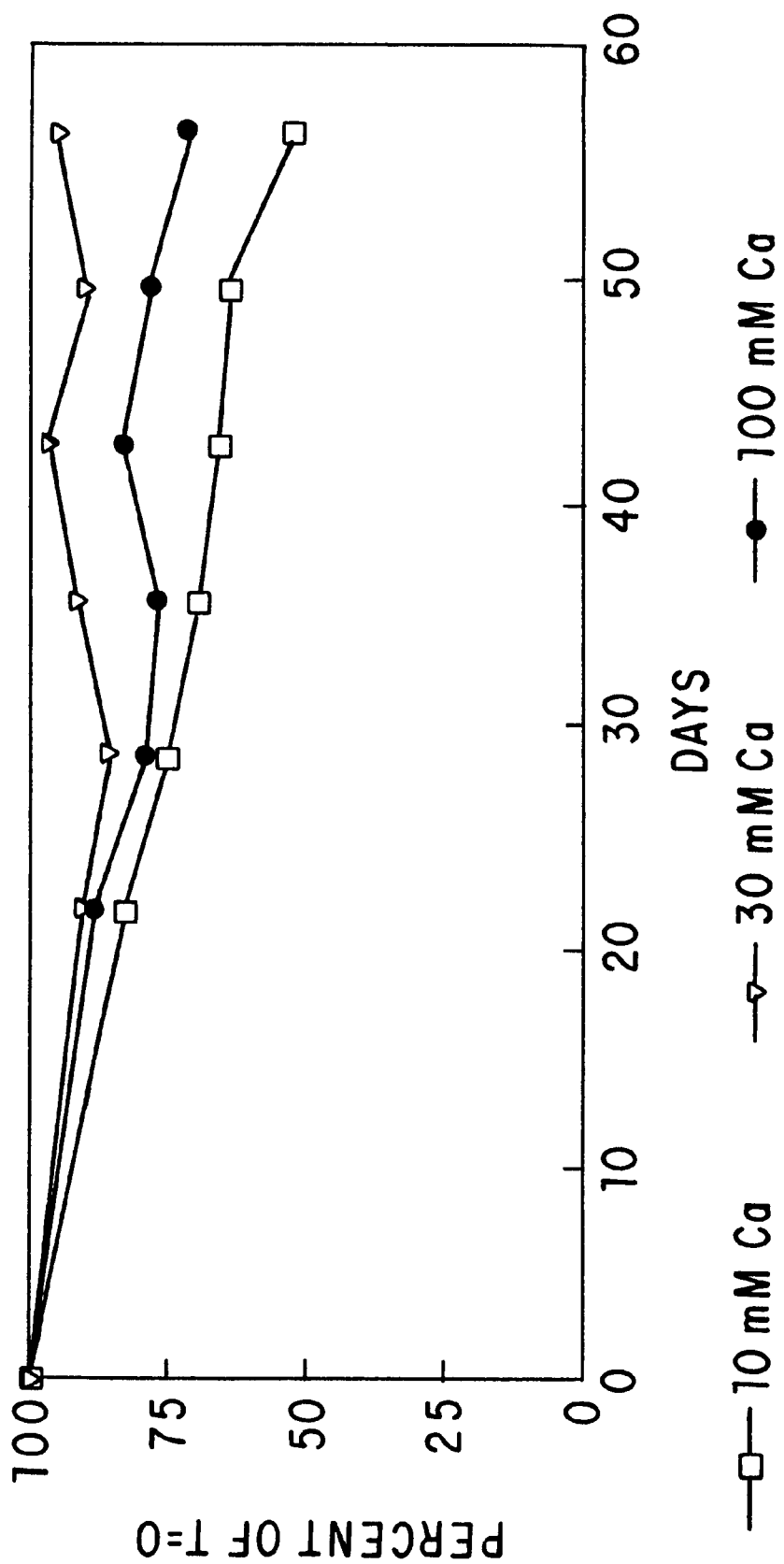

FIG. 13. FIX Stability at pH 6.2 with varying concentrations of $CaCl_2$ at 37° C. Data from Example 6 are graphed here. The shallower decay curve observed with 100 mM $CaCl_2$ may reflect activation and clear activation was observed with 30 mM $CaCl_2$.

FIGS. 14A–14M: SDS-PAGE. Data from Example 6 are shown. SDS-PAGE gels with Coomassie blue staining are shown in FIG. 14A–14D for 0 and 56 days, and in FIGS. 14E–14M (reduced gels) for all time points, for all pH/$CaCl_2$ combinations tested.

Figure 14A:
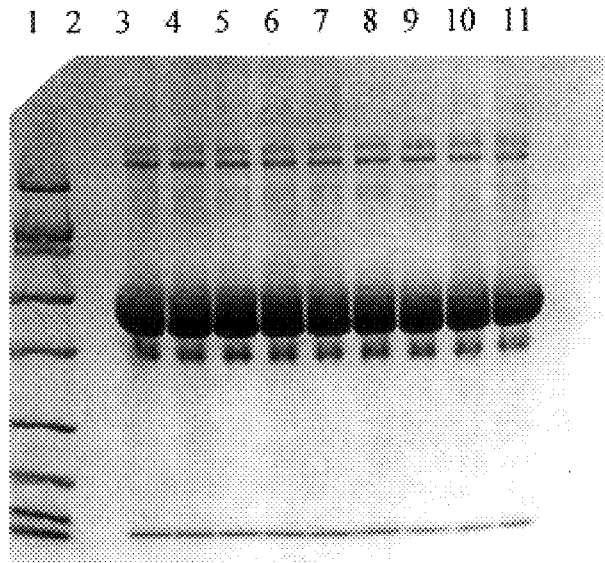
Figure 14B:
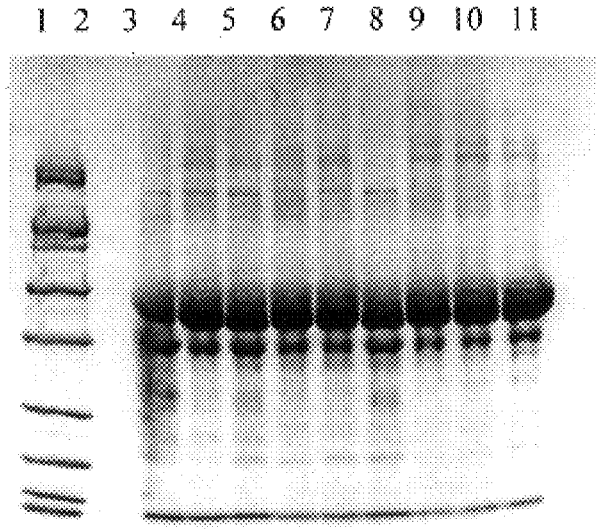
Figure 14C:
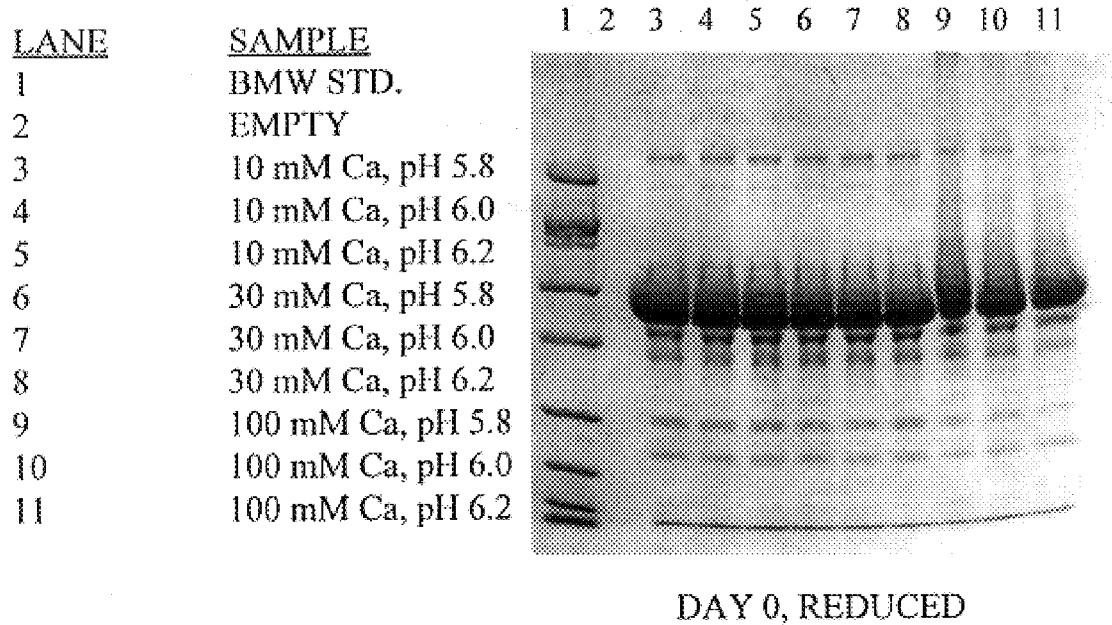
Figure 14D:
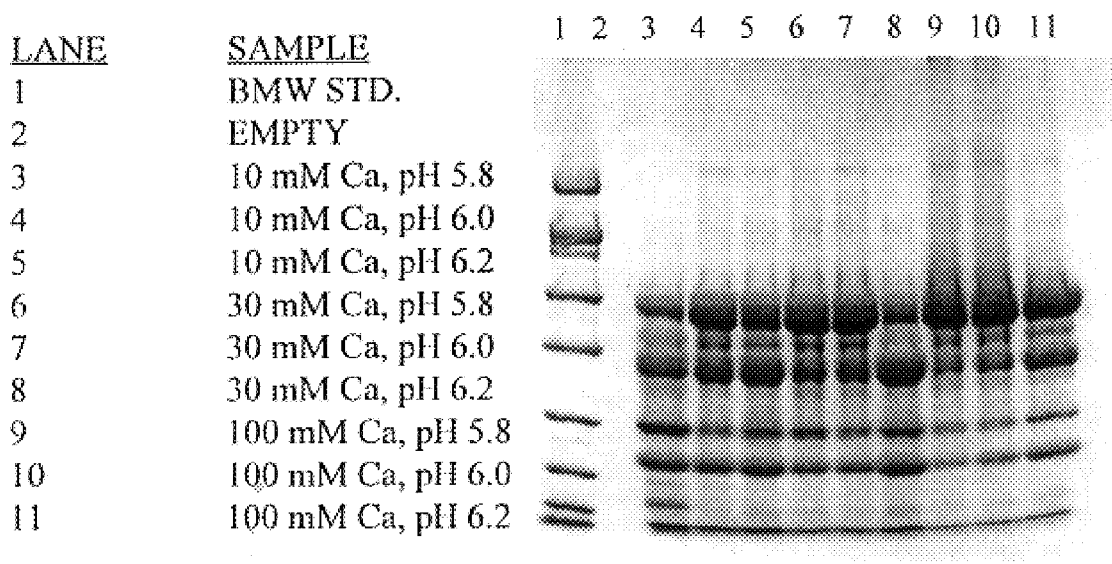
Figure 14E:
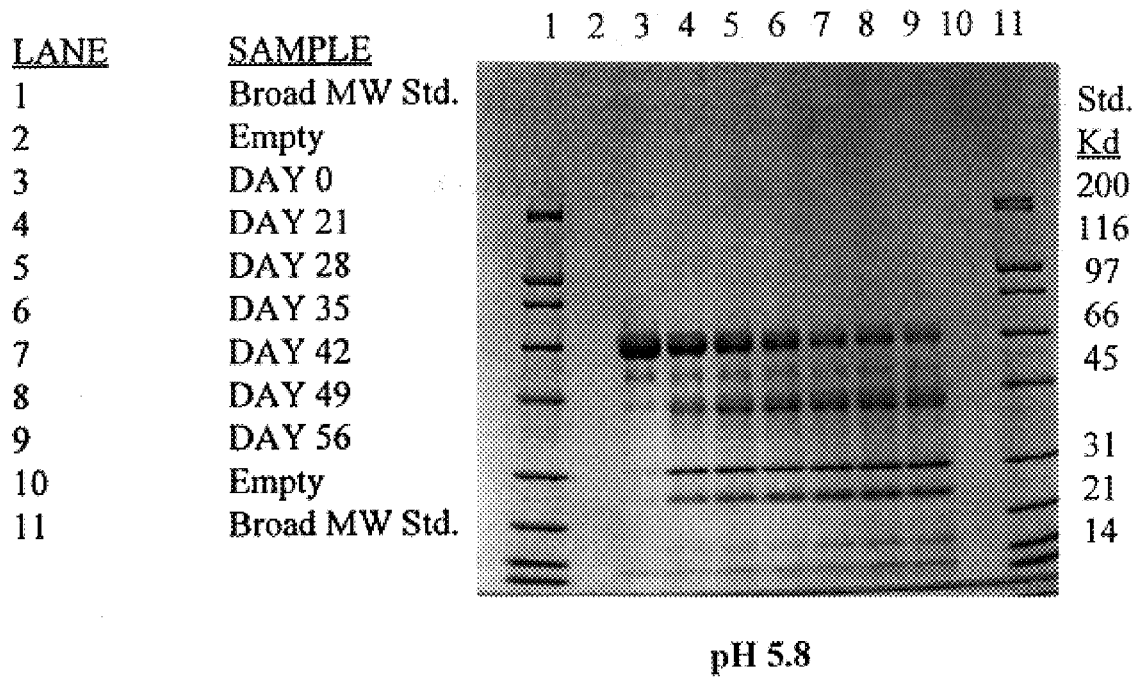
Figure 14F:
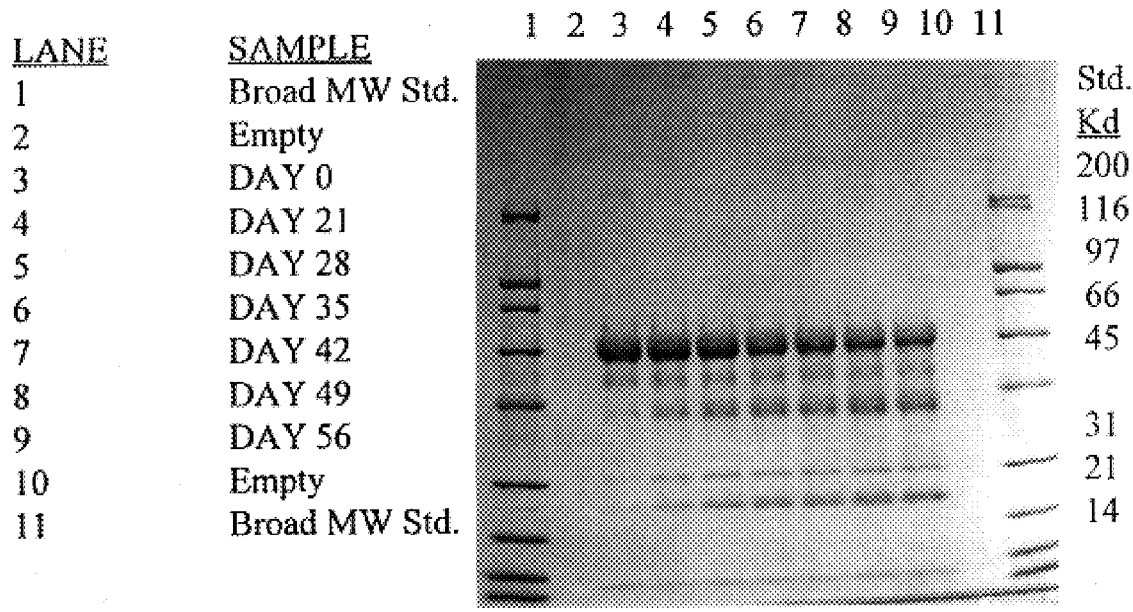
Figure 14G:
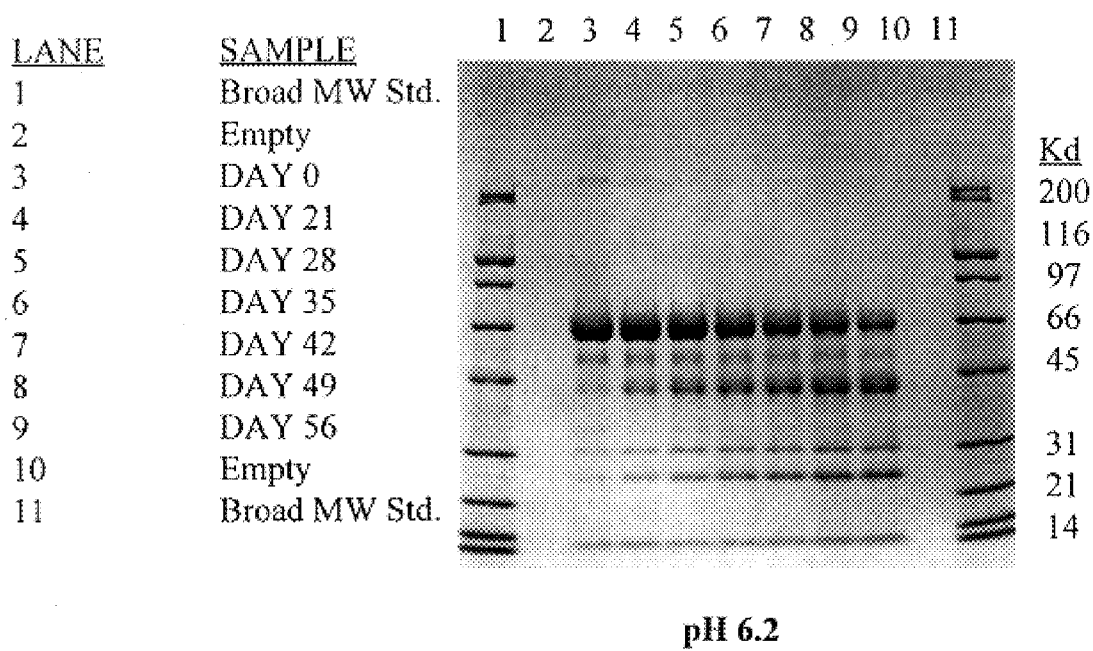
Figure 14H:
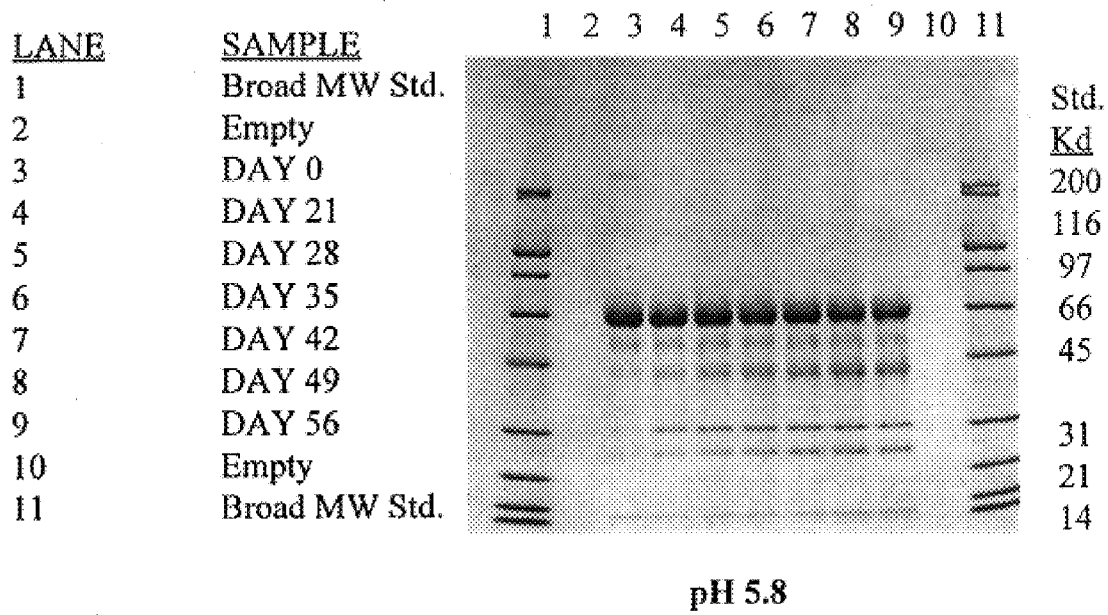
Figure 14I:
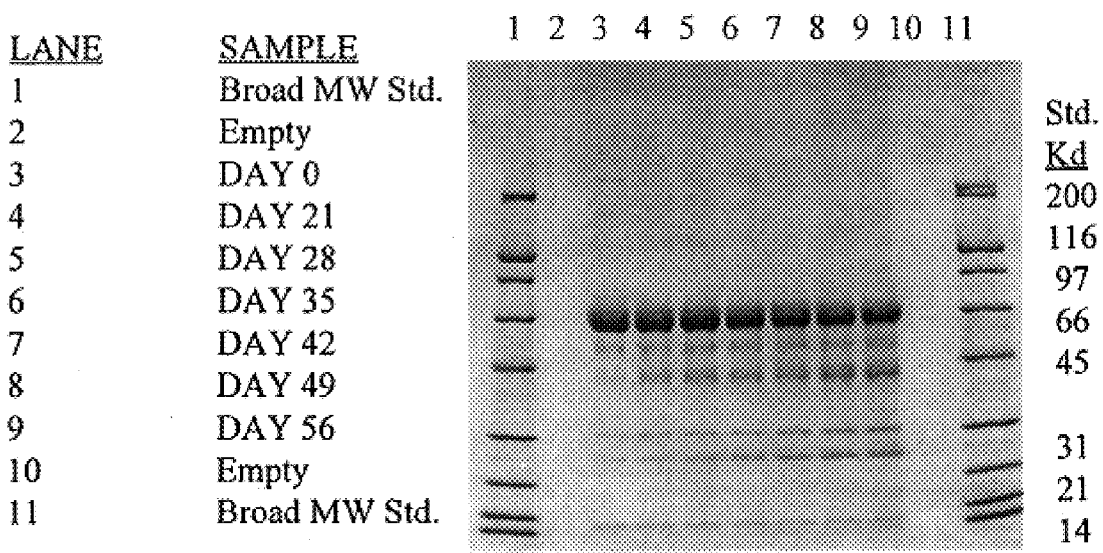
Figure 14J:
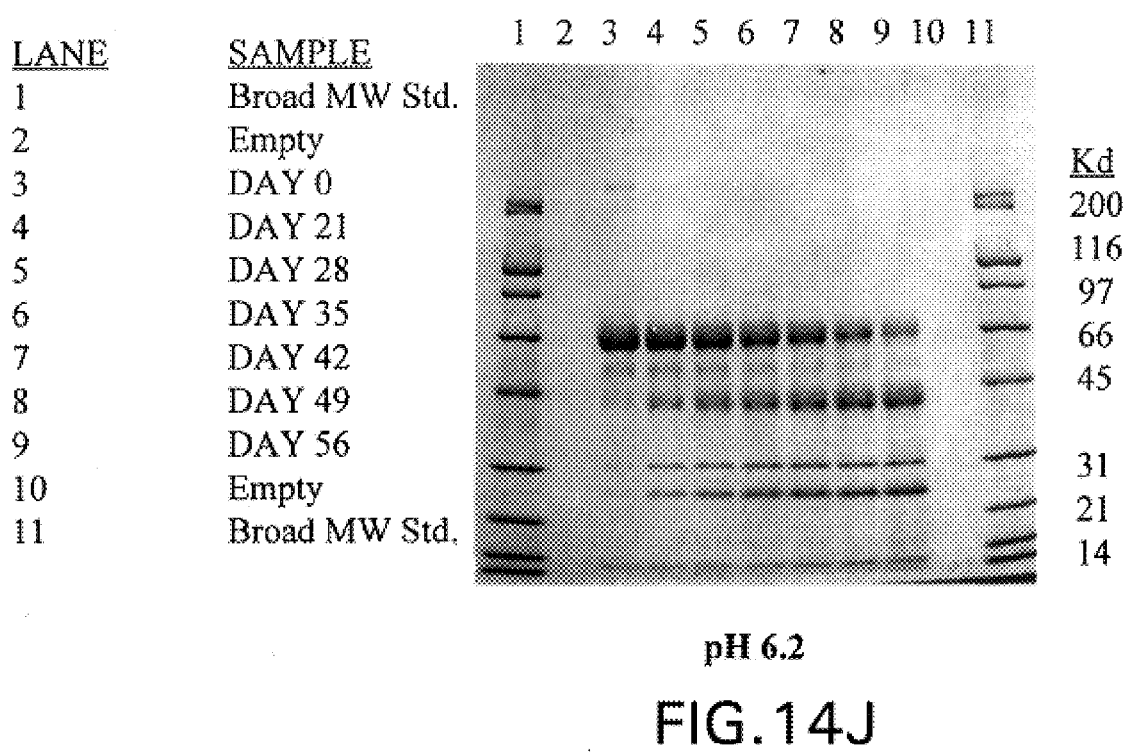

In FIG. 14A–14D, the lanes are as follows: 1, broad molecular weight (MW) standard; 2, empty; 3, 10 mM Ca, pH 5.8; 4, 10 mM Ca, pH 6.0; 5, 10 mM Ca, pH 6.2; 6,30 mM Ca, pH 5.8; 7,30 mM Ca, pH 6.0; 8,30 mM Ca, pH 6.2; 9, 100 mM Ca, pH 5.8; 10,100 mM Ca, pH 6.0 ; and 11, 100 mM Ca, pH 6.2. In FIG. 14B–14D, the lanes are as follows: 1, broad MW standard; 2, empty; 3, day 0;4, day 21; 5, day 28; 6, day 35;7, day 42;8, day 49;9, day 56; 10, empty; and 11, broad MW standard.

Figure 14K:
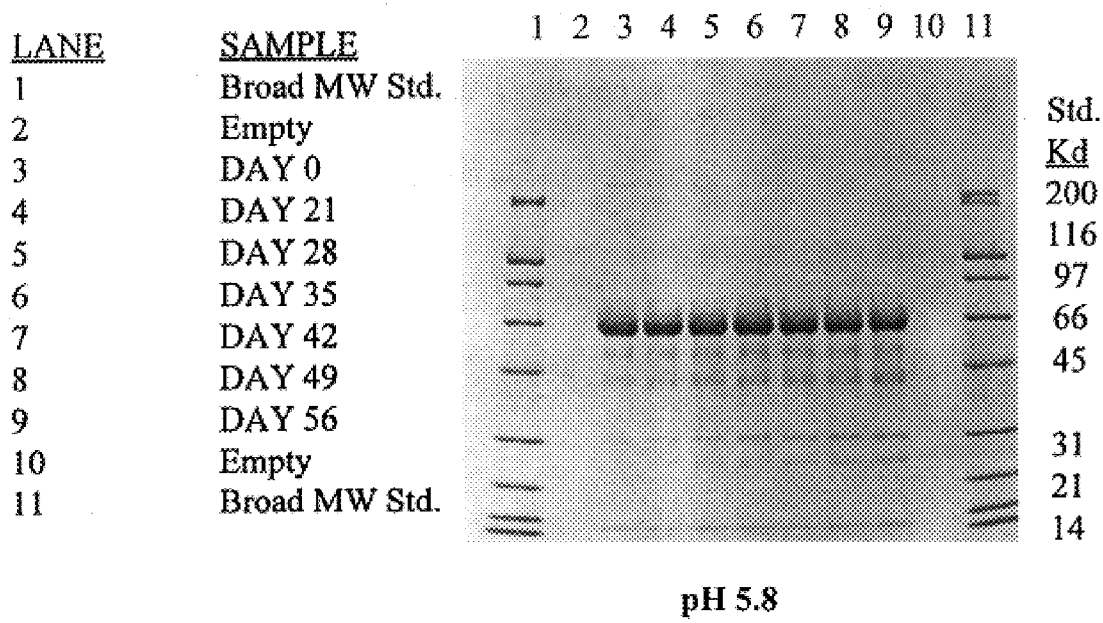
Figure 14L:
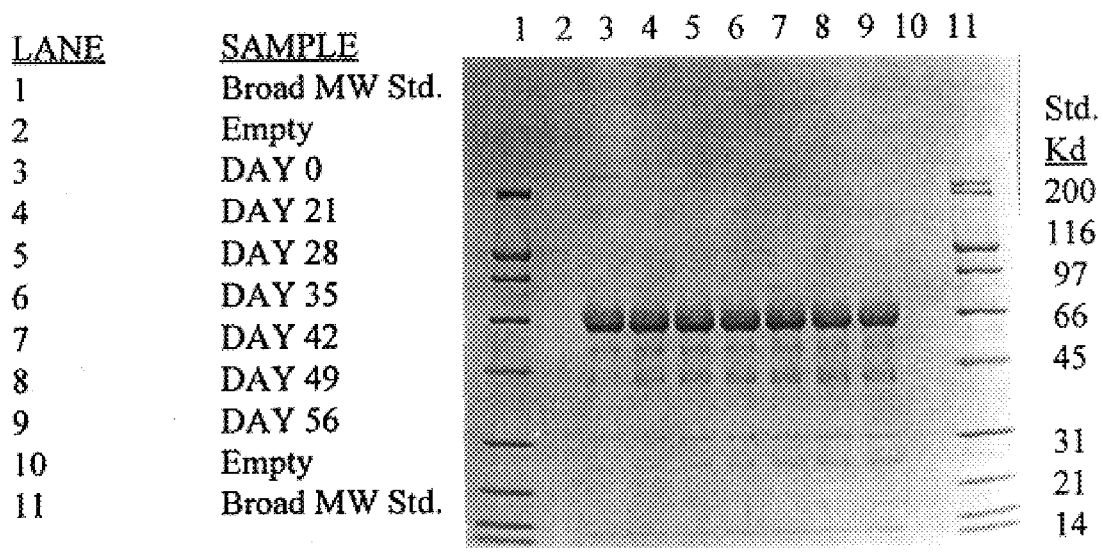
Figure 14M:
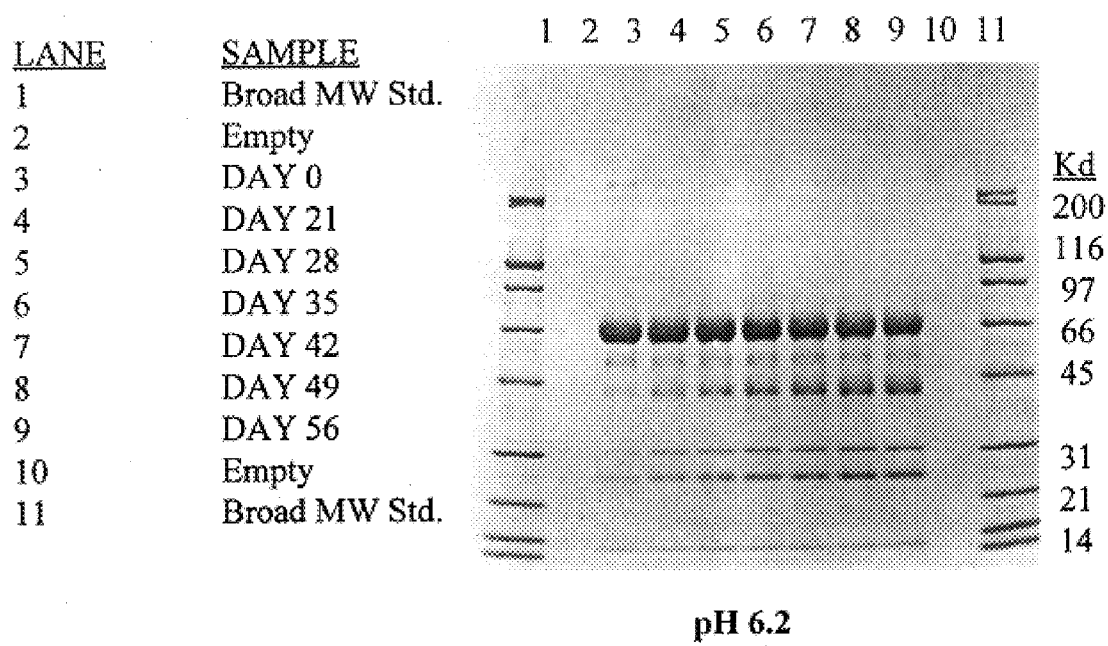

At zero time, Factor IX appeared the same in all formulations, except that in 100 mM $CaCl_2$ there was high molecular weight smearing in the reduced gels probably due to non-specific salt effects. High molecular weight smearing was not seen when the 100 mM $CaCl_2$ samples were diluted with water (FIG. 14K–14M). At 56 days, there was fragmentation in all samples, especially evident in the reduced gels. More fragmentation is observed in lanes 3, 5 and 8 of FIG. 14A–14D (10 mM CaCl$_2$ at pH 5.8 and pH 6.2 and 30 mM CaCl$_2$ at pH 6.2).

Figure 15:
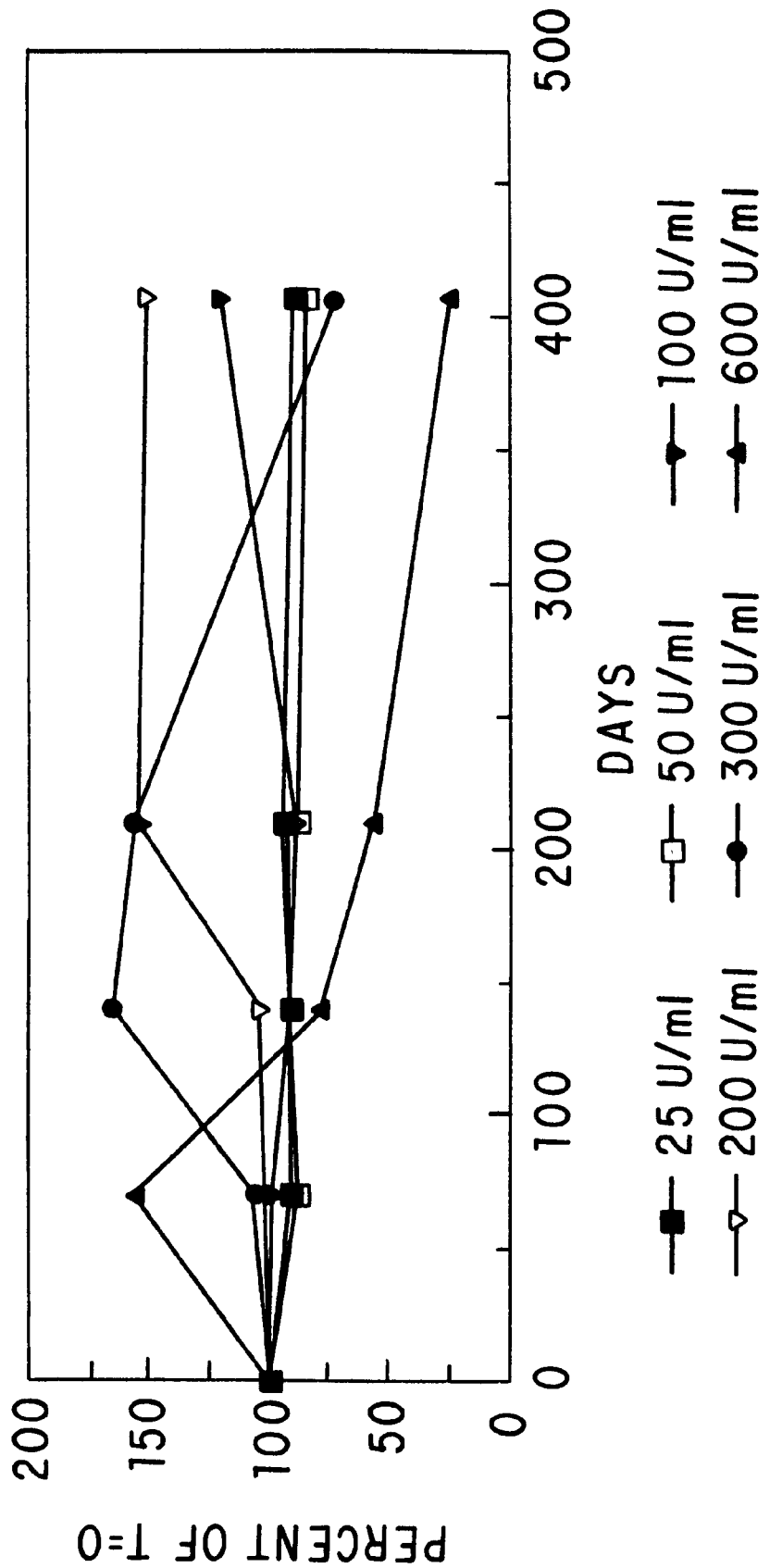

FIG. 15. FIX Stability with 10 mM CaCl$_2$ at 4° C. Data from Example 7 are graphed here. Elevation of clotting activity above the initial 100% value, indicative of activation, is observed at 600 units/mL (70 days), 300 units/mL (140 days), 200 units/mL (210 days), and 100 units/mL (410 days). No evidence of activation is observed at 25 units/mL or 50 units/mL after 410 days. At the 410 day point, >80% of activity remained in these samples.

Figure 16:
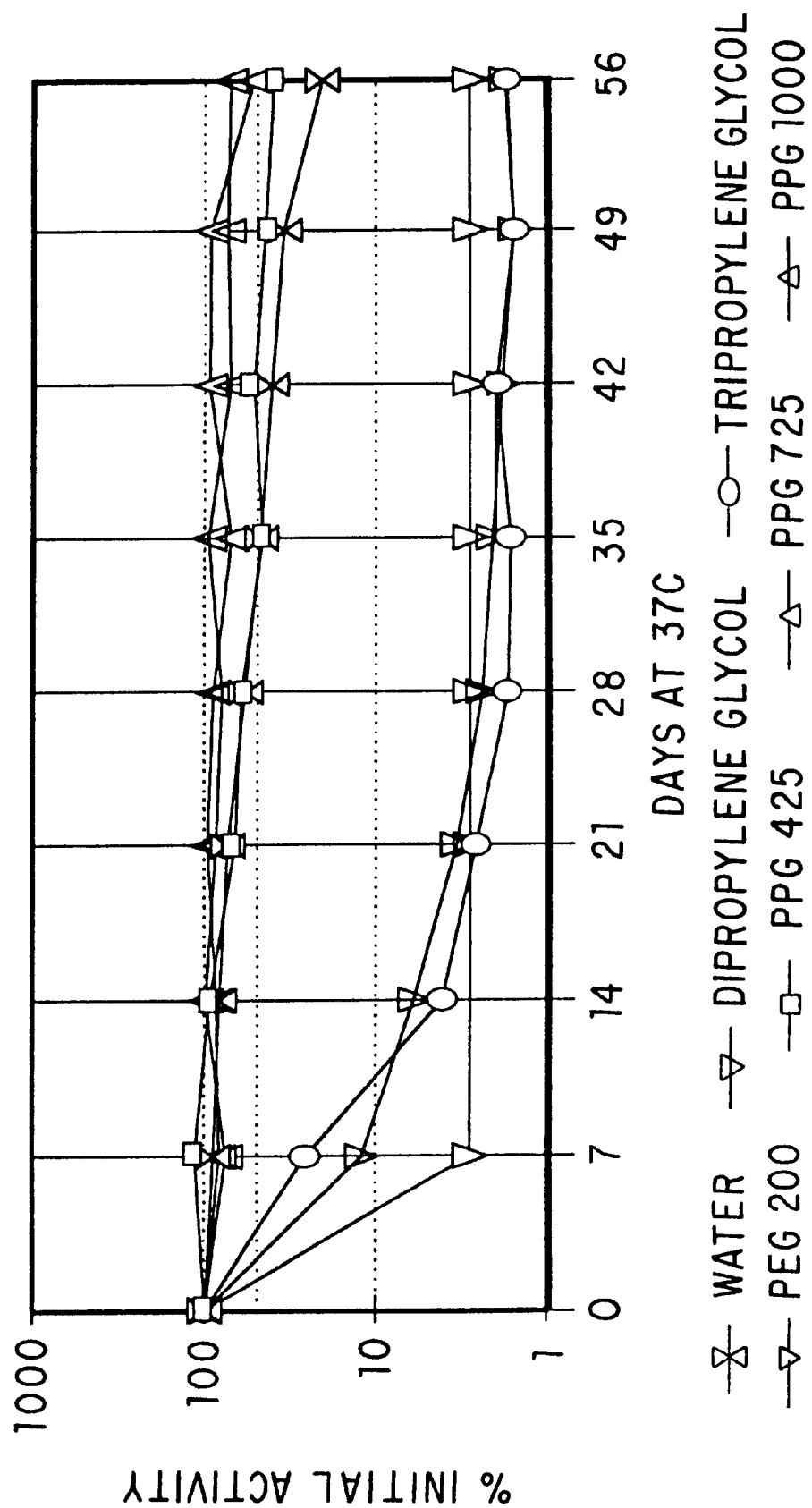

FIG. 16. Lyophilized FVIII Stability at 37° C. in Non-aqueous Liquid Formulations. Data from Example 8 are graphed here.

Figure 17:
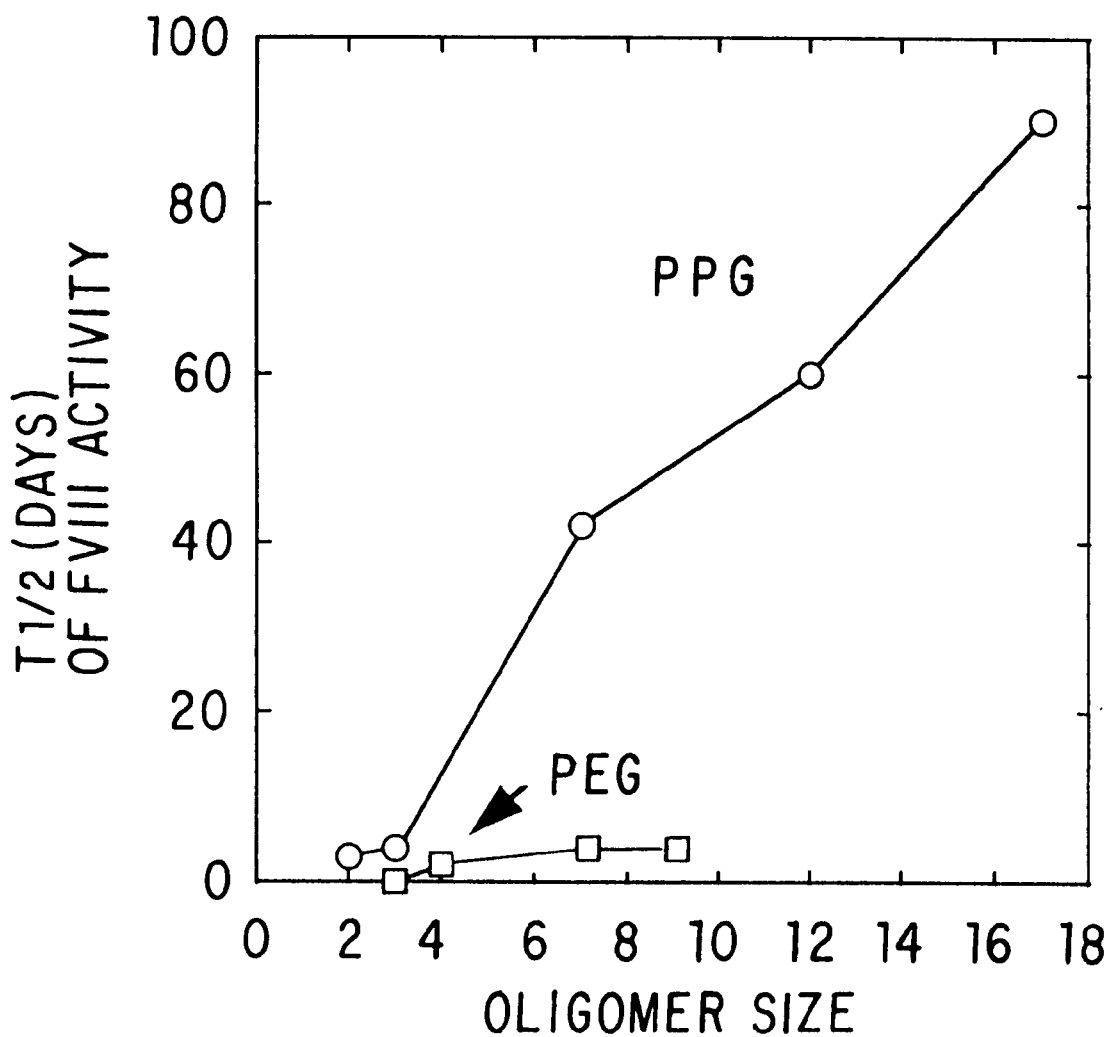

FIG. 17. FVIII Stability Correlates with Polypropylene Oligomer Size. When plotted against PPG oligomer size (i.e., the number of monomer units making up the polypropylene glycol), the half-life values observed are nearly linear with oligomer size up to PPG 1000 (which contains an avaerage of 17 monomer units).

Figure 18:
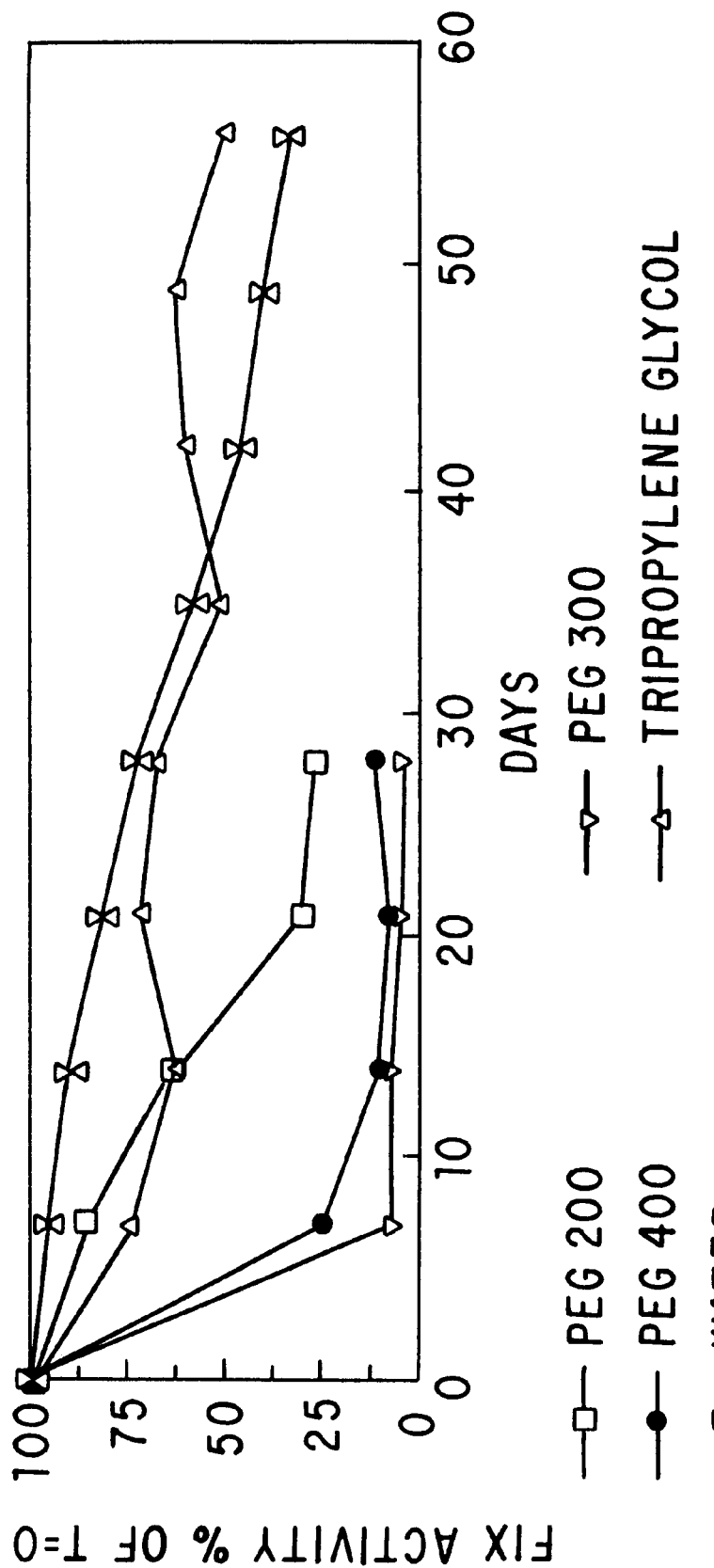
Figure 19:
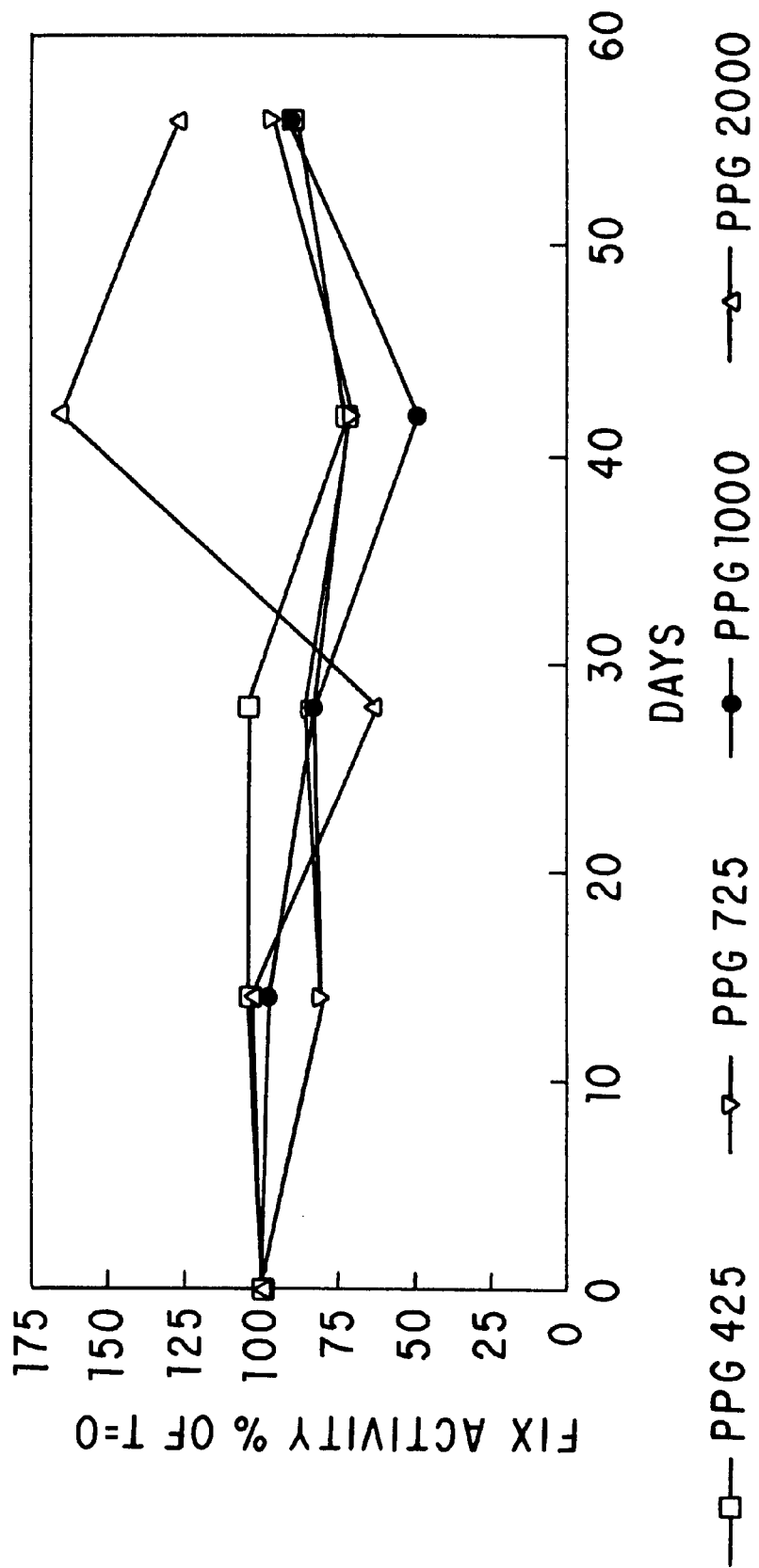

FIG. 18, FIG. 19. Lyophilized FIX Stability at 37° C. in Non-aqueous Liquid Formulations. Data from Example 9 are graphed here. FIG. 18 shows data obtained with water, tripropylene glycol and various polyethylene glycols. FIG. 19 shows data obtained with various polypropylene glycols.

Figure 20:
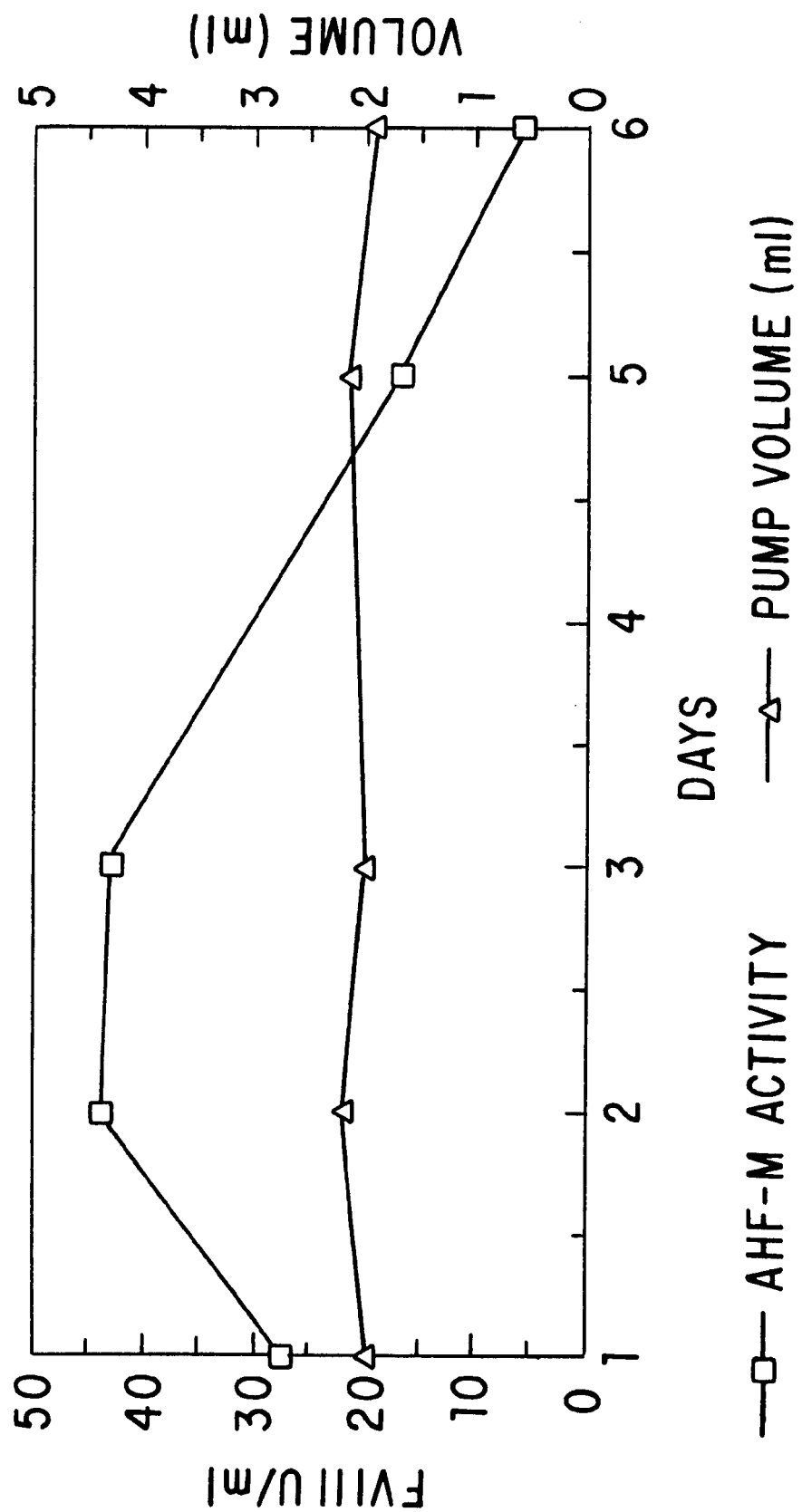

FIG. 20. In Vitro Release of Factor VIII (AHF-M) using an Arrow Model 3000 Implantable Pump. Data from Example 10 are graphed here. As seen in the graph, Factor VIII activity was 95% lost by day 6. This was determined to be caused, however, by bacterial contamination when sterility was compromised during the process of filling the pump with AHF-M solution (bacterial contamination was confirmed by agar plate colony and culture assessment).

Figure 21:
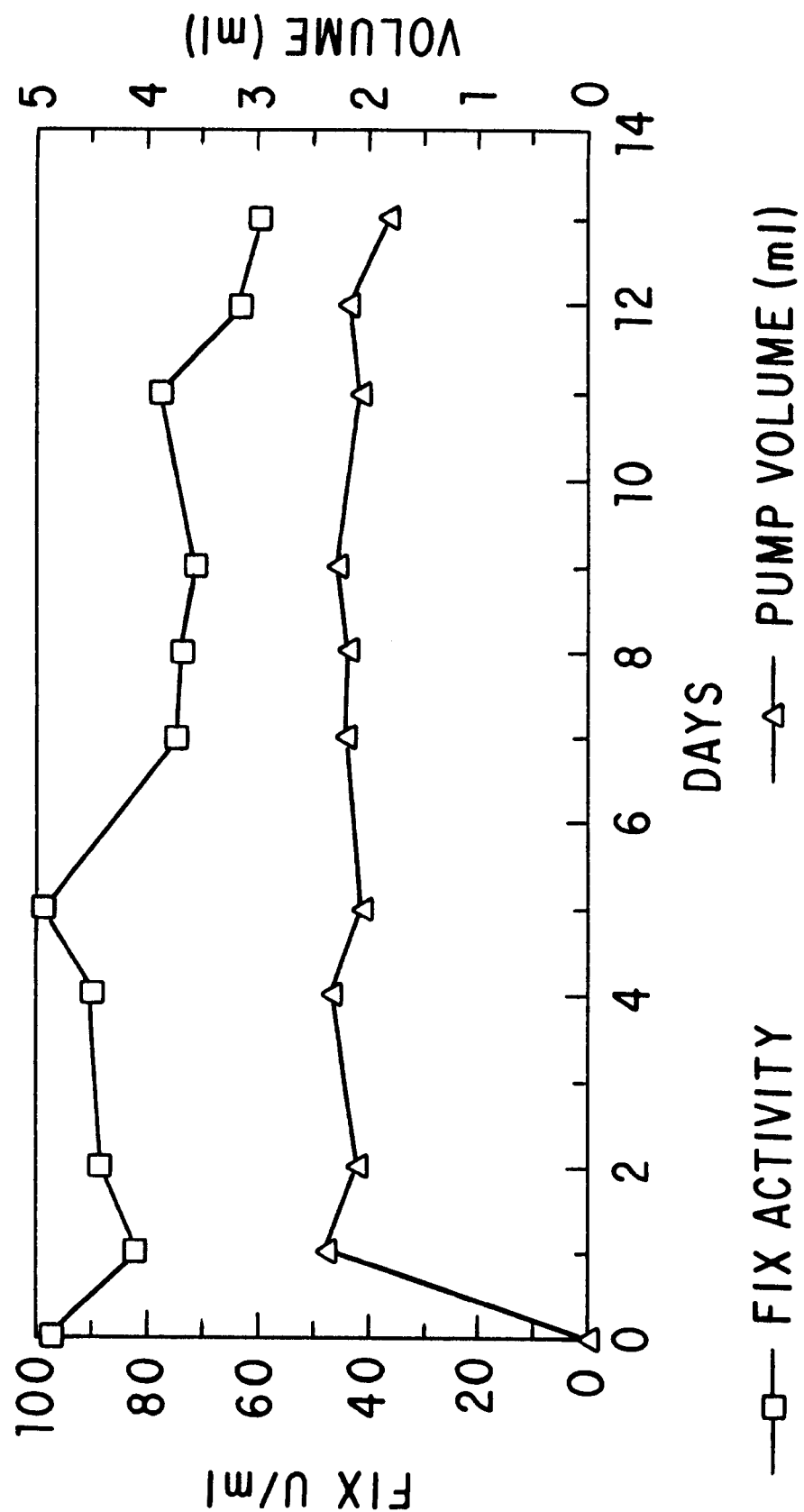

FIG. 21. In Vitro Release of Factor IX at 37° C. using an Arrow Model 3000 Implantable Pump. Data from Example 10 are graphed here. As seen in the graph, Factor IX activity in the effluent from the pump decreased relatively steadily throughout the 13 days of operation. The half-life was 18–20 days, about half that observed in polypropylene tubes, At day 13, the effluent activity was 60% of the starting activity. No bacteria were detected in the Factor IX effluent.

Figure 22:
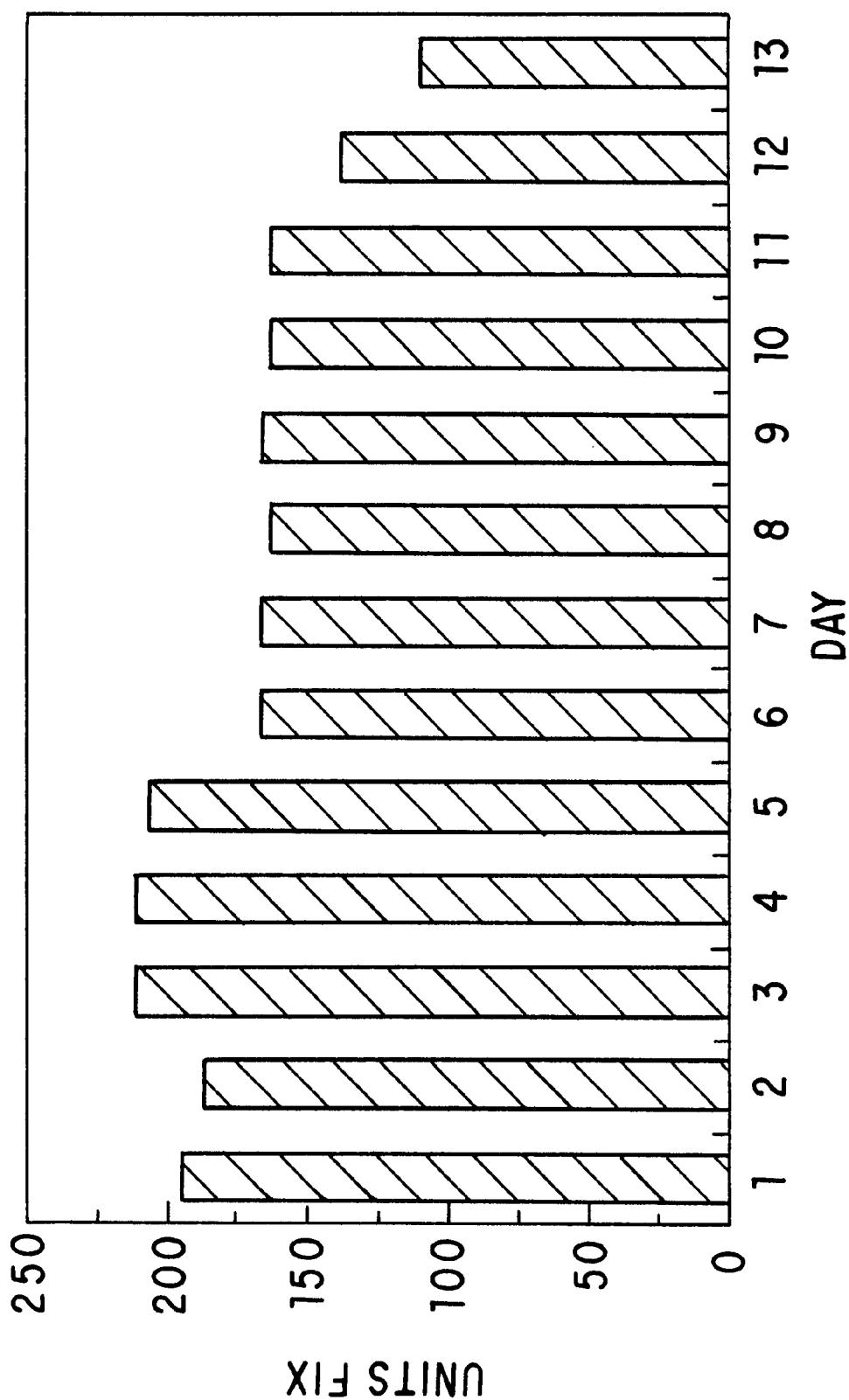

FIG. 22. Units of Factor IX-M Delivered In vitro using an Arrow Model 3000 Implantable Pump. Data from Example 10 are graphed here. Effluent volume was maintained accurately at 2 mL/day. The units of Factor IX delivered per day was 185–210 units for the first five days, decreasing to 160–170 units during days 6–11 and decreasing further to 110–140 units for the final two days.

Figure 23:
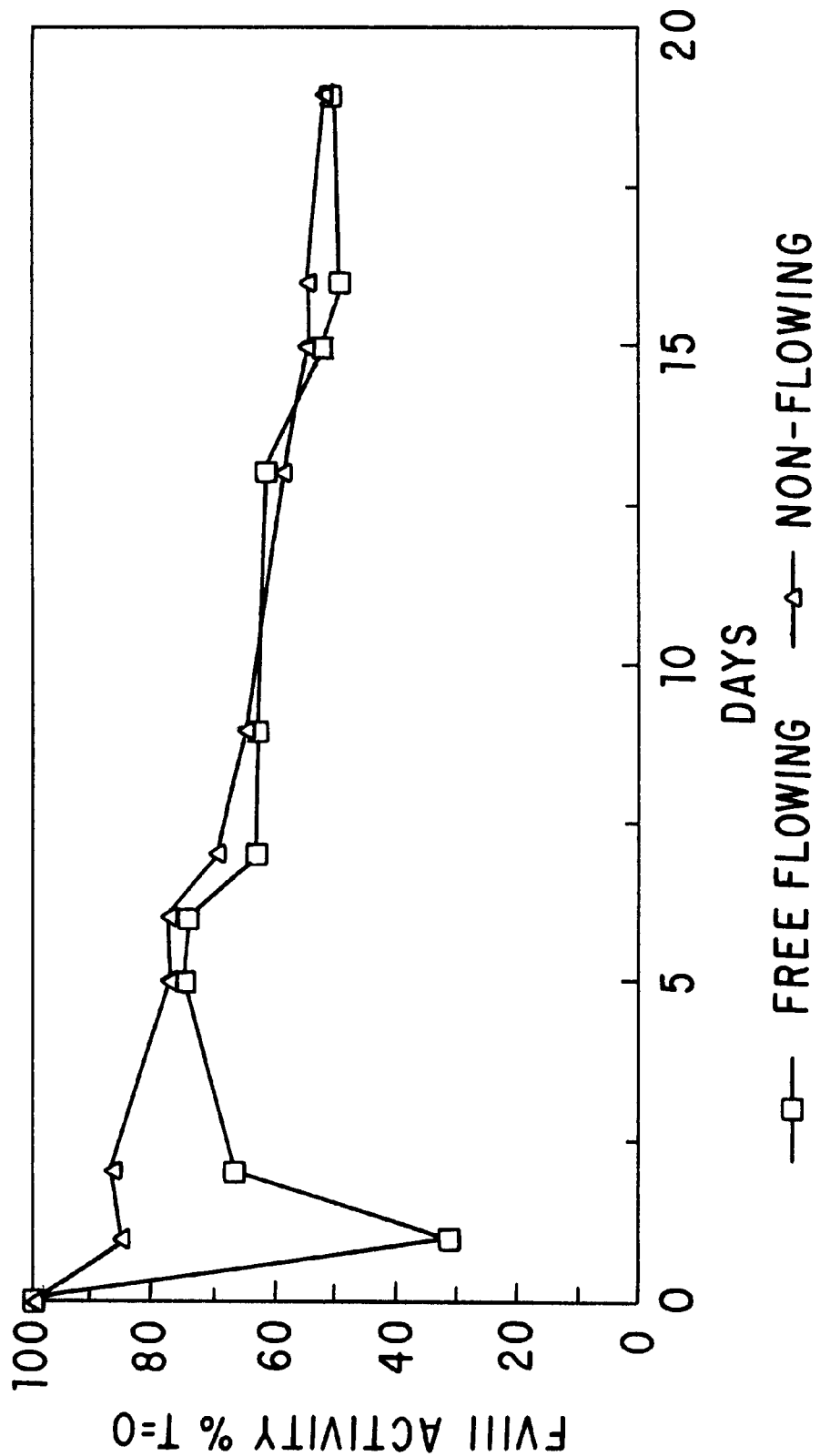

FIG. 23. AHF-M Stability at 37° C. in Arrow Model 3000 Implantable Pumps. Data from Example 11 are graphed here. The activity of Factor VIII samples which were allowed to flow from the pump and those taken from the pump reservoir under stasis did not differ significantly (the dip in the first samples of pump effluent was due to dilution of the effluent with the saline solution used to purge the pump tubing). This suggests that the glass and rubber surfaces do not alter the activity of the Factor VIII exiting the pump.

Figure 24:
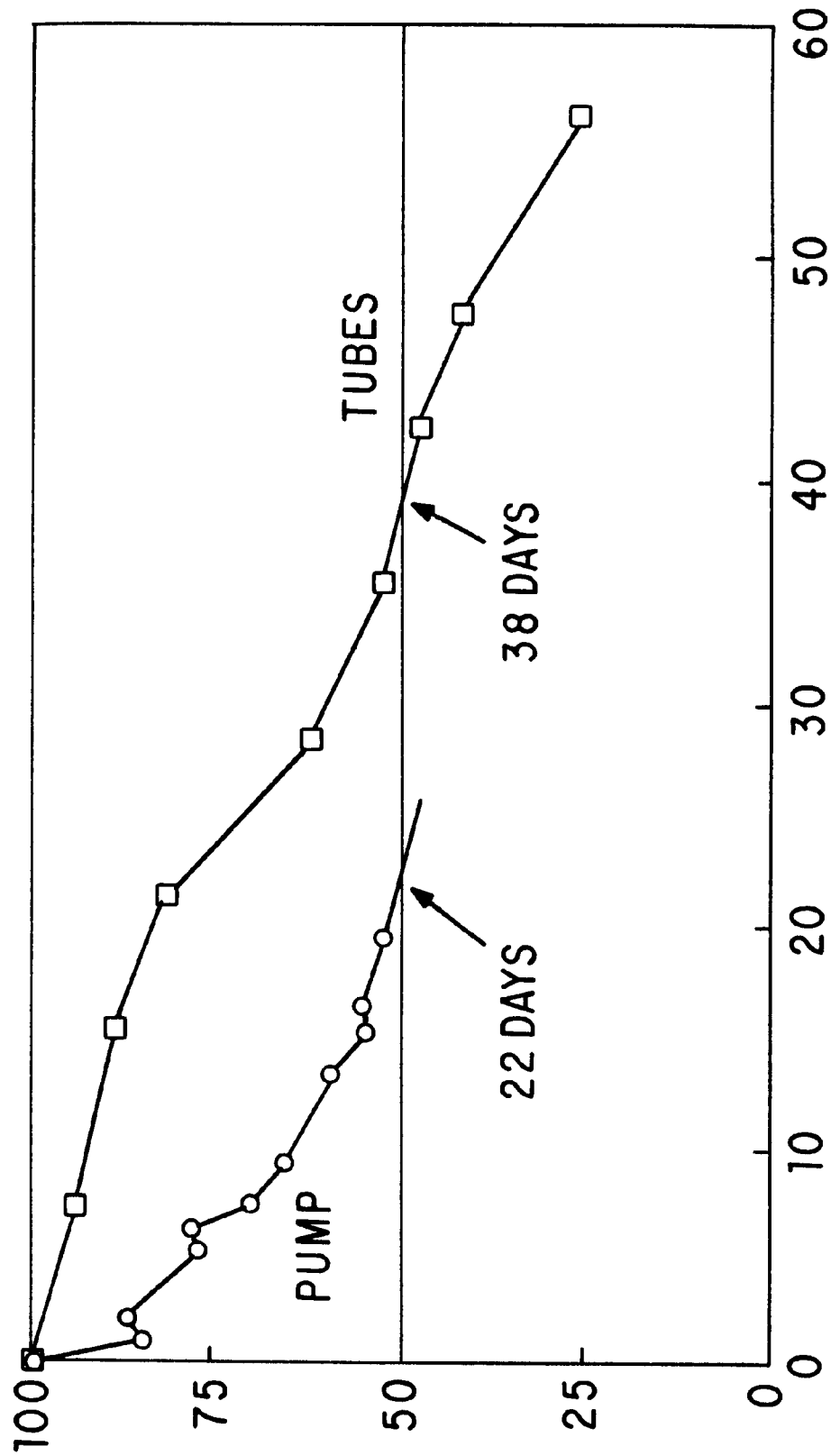

FIG. 24. AHF-M Stability at 37° C. in Arrow Model 3000 Implantable Pump compared to Polypropylene Tube. Data from Example 11 are graphed here. When the decay curve for Factor VIII sampled from the titanium pump reservoir under static conditions was compared to the decay curve for Factor VIII incubated in polypropylene tubes in an earlier experiment, the decay was more rapid in the pump than in the polypropylene tubes. The lower observed stability of Factor VIII incubated at 37° C. in the titanium reservoir of the Arrow Model 3000 pump compared to the observed stability of Factor VIII incubated at 37° C. in polypropylene tubes suggests a difference in the biocompatibility of these two materials with Factor VIII.

Figure 25:
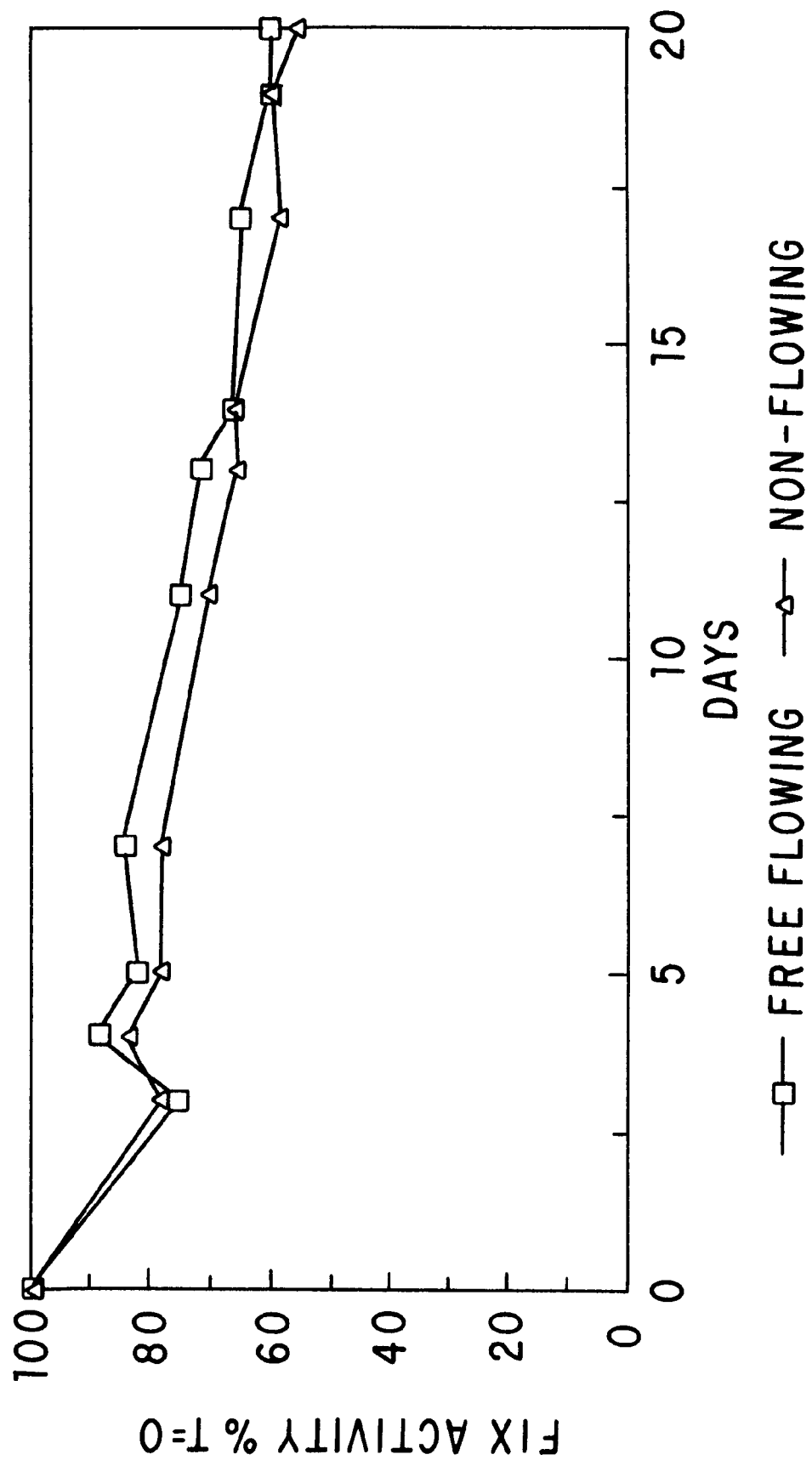

FIG. 25. Factor IX-M Stability at 37° C. in Arrow Model 3000 Implantable Pumps. Data from Example 12 are graphed here. The activity of Factor IX samples which were allowed to flow from the pump and those taken from the pump reservoir under stasis did not differ significantly. As with Factor VIII, no difference was observed between Factor IX held statically inside the pump reservoir and Factor IX pumped out through the glass/silicone rubber exit catheter, indicating that glass and silicone rubber do not alter the potency of the Factor IX exiting the pump.

Figure 26:
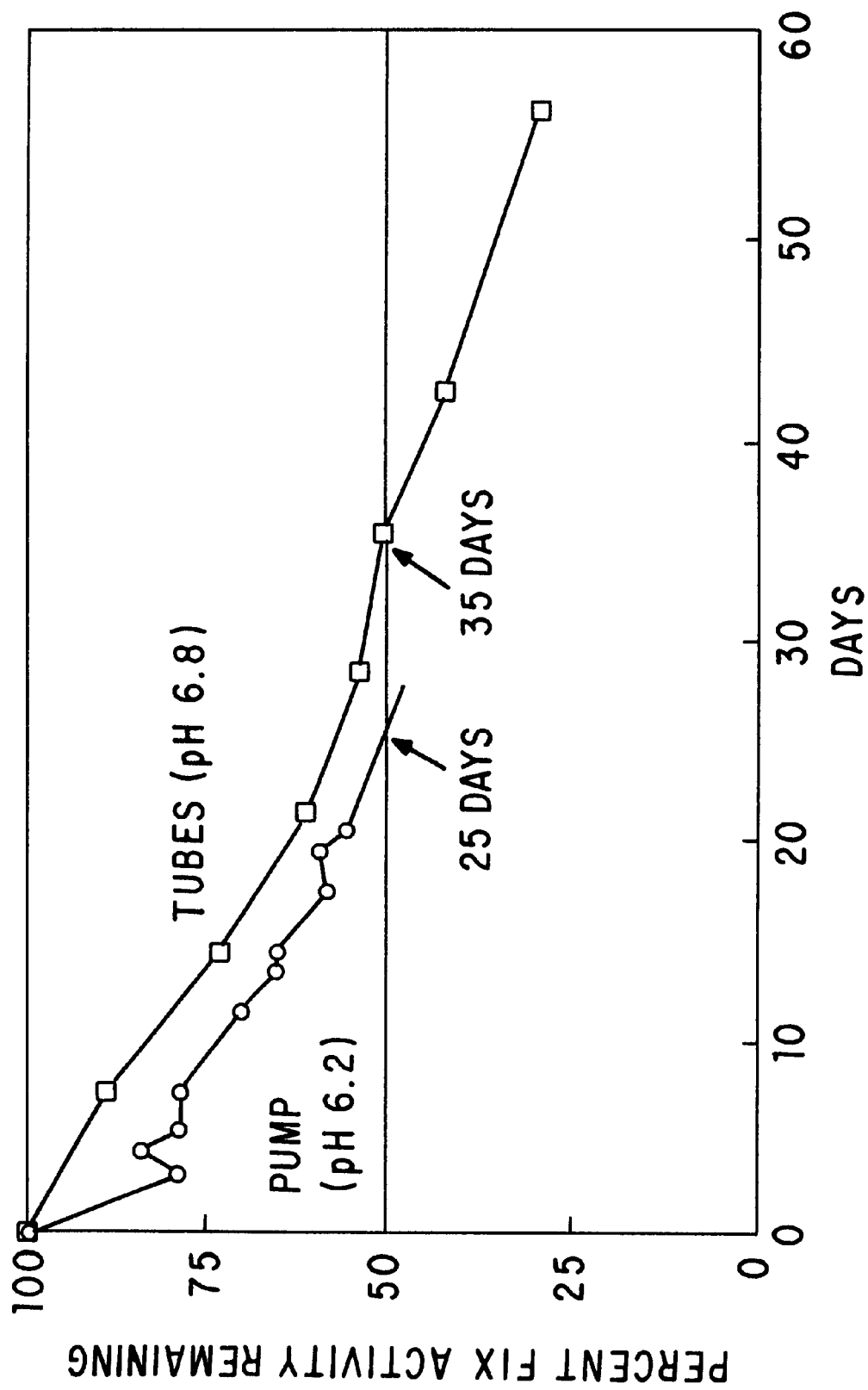

FIG. 26. Factor IX-M in histidine/NaCl/CaCl$_2$ Solution at 37° C. in Arrow Model 3000 Implantable Pump compared to Polypropylene Tube. Data from Example 12 are graphed here. When the decay curve for Factor IX sampled from the titanium pump reservoir under static conditions was compared to the decay curve for Factor IX incubated in polypropylene tubes in an earlier experiment, the in vitro half-life in the titanium reservoir was approximately 25 days, compared to a half-life of about 35 days in polypropylene tubes. The lower half-life of Factor IX in the titanium reservoir appears to be due to an initial drop (about 25%) in Factor IX activity at the time of the first assay (day 2), suggesting that a portion of the Factor IX is bound to the inner surface of the pump reservoir but the remainder is unaffected.

V. DETAILED DESCRIPTION OF THE PREFERRED EMBODIMENTS

A. DEFINITIONS

Unless defined otherwise, all technical and scientific terms used herein have the same meaning as is commonly understood by one of skill in the art to which this invention belongs. All patents and publications mentioned herein are incorporated by reference.

"Plasma" as used herein refers to the fluid, non-cellular portion of the blood of humans or animals as found prior to coagulation. It is distinguished from serum, which is obtained after coagulation.

"Plasma protein" as used herein refers to the soluble proteins found in the plasma of normal humans or animals. These include but are not limited to coagulation proteins, antibodies, albumin, lipoproteins, complement proteins, and the like.

"Vitamin K-dependent plasma proteins" as used herein refer to those proteins found in the plasma of a normal individual or animal that are members of the coagulation cascade, either as procoagulants or anticoagulants, and whose synthesis requires the presence of vitamin K. These are present in proenzyme form or activated form. Vitamin K-dependent plasma proteins include: Factor II; Factor VII; Factor IX; Factor X; Protein C; Protein S; and Protein Z.

"Non-vitamin K-dependent plasma proteins" as used herein refer to those proteins found in the plasma of a normal individual or animal that are members of the coagulation cascade, either as procoagulants, anticoagulants, or cofactors, and whose synthesis does not require the presence of vitamin K. These are present in proenzyme form, non-activated cofactor form, or activated form. Non-vitamin K-dependent plasma proteins include Factor VIII and von Willebrand's factor.

"Factor IX" (or "coagulation Factor IX") as used herein refers to a plasma glycoprotein that is a member of the intrinsic coagulation pathway and is essential to blood coagulation. A congenital X-linked deficiency of biologically active Factor IX results in Hemophilia B, a potentially life-threatening disorder.

"Factor VIII" (or "coagulation Factor VIII") as used herein refers to a plasma glycoprotein that is a member of the intrinsic coagulation pathway and is essential to blood coagulation. A congenital X-linked deficiency of biologically active Factor IX results in Hemophilia A, a potentially life-threatening disorder.

"Liquid formulation" as used herein refers to a composition of matter that is found as a liquid, characterized by free movement of the constituent molecules among themselves but without the tendency to separate. Liquid formulations include aqueous and non-aqueous liquids.

"Aqueous liquid formulation" as used herein refers to a liquid composition that contains water as a component.

"Non-aqueous liquid formulation" as used herein refers to a liquid composition that does not contain water as a component.

"Hydrophilic non-aqueous liquid formulation" as used herein refers to a liquid composition that does not contain water as a component and that contains liquids that have a strong affinity for water.

"Mixed aqueous/non-aqueous liquid formulation" as used herein refers to a liquid composition that contains a mixture of water and an additional liquid composition.

"Body temperature" as used herein refers to the normal physiological temperature of a human or animal. The average body temperature of a human is 37° Centigrade (C.).

"Refrigeration temperature" as used herein refers to the temperature for cold storage that does not allow freezing. One refrigeration temperature is 4° Centigrade (C.).

"Reconstitution" as used herein refers to the dissolution or resuspension of a solid material into a liquid solution or suspension by the addition of a liquid.

"Rehydration" as used herein refers to the reconstitution to a liquid state by the addition of water.

"Prophylaxis" as used herein refers to the administration of treatment to prevent the onset of symptoms.

"Continuous delivery" as used herein refers to the uninterrupted introduction of a material into the body of a human or animal.

"Injection" as used herein refers to the introduction of a liquid by force into the body of a human or animal.

"Hydrogel" as used herein refers to a semisolid composition constituting a substantial proportion of water, and in which polymers or mixtures thereof are dissolved or dispersed.

"Intranasal delivery" as used herein refers to the introduction of material into the body of a human or animal by absorption through the mucous membranes of the nasal passages and sinuses.

"Inhalation delivery" as used herein refers to the introduction of material into the body of a human or animal by absorption through the lungs.

"Oral delivery" as used herein refers to the introduction of a material into the body of a human or animal by ingestion through the mouth.

"Parenteral delivery" as used herein refers to modes of administration which include intravenous, intramuscular, intraperitoneal, intrasternal, subcutaneous and intraarticular injection and infusion.

"Stability" as used herein refers to the retention of those characteristics of a material that determine activity and/or function.

"Pharmaceutically acceptable carrier" as used herein refers to a nontoxic solid, semisolid or liquid filler, diluent, encapsulating material or formulation auxiliary of any type.

"Patient" as used herein refers to human or animal individuals receiving medical care and/or treatment.

"Congenital deficiency" as used herein refers to the condition of an individual that lacks, as a result of heredity, a compound found in normal individuals. Congenital deficiencies are permanent absent transplantation or genetic intervention, which at this time are not guaranteed cures.

"Acquired deficiency" as used herein refers to the condition of an individual that lacks, as a result of a non-congenital influence, a compound found in normal individuals. Acquired deficiencies are frequently the transient result of other conditions or their treatment, but are nonetheless debilitating and life threatening.

B. PREFERRED EMBODIMENTS

A first preferred embodiment of the present invention is directed to a stable liquid formulation containing one or more plasma proteins. Preferably, the stable liquid formulation of the present invention is stable, i.e., at least 50% of the activity of the plasma protein(s) contained in the formulation is maintained, for at least one day (24 hours), more preferably for at least 13 days, and most preferably for at least 30 days at 37° C. or for at least 540 days at 4° C. The activity of plasma proteins may be determined according to any of the methods and techniques known to those skilled in the art.

According to this embodiment of the present invention, any plasma protein may be contained in the stable liquid formulation. These plasma proteins may be in the form of proenzymes or cofactors that have not yet been activated or they may be in the activated form. Suitable plasma proteins may be obtained from human or mammalian plasma by any of the purification methods known and available to those skilled in the art; from supernatants or pastes of recombinant tissue culture, viruses, yeast, bacteria, or the like that contain a gene that expresses a human or mammalian plasma protein which has been introduced according to standard recombinant DNA techniques; or from the fluids (e.g. blood, milk, lymph, urine or the like) of transgenic animals that contain a gene that expresses a human plasma protein which has been introduced according to standard transgenic techniques. The inventive liquid formulation may optionally further contain one or more additional proteins as desired, including: other plasma proteins; protease inhibitors, such as thrombin inhibitors; carrier proteins, including but not limited to von Willebrand Factor; peptides; and derivatives thereof.

In a particularly preferred embodiment of the present invention, the plasma protein is a vitamin K-dependent plasma protein. Illustrative examples of such vitamin K-dependent plasma proteins include, but are not limited to, Factor II, Factor VII, Factor IX, Factor X, Protein C, Protein S and Protein Z. Preferably, the vitamin K-dependent plasma protein is Factor IX.

In another particularly preferred embodiment of the present invention, the plasma protein is a non-vitamin K-dependent plasma protein. Non-vitamin K-dependent plasma proteins include, but are not limited to, Factor VIII and von Willebrand's factor. Preferably, the non-vitamin K-dependent plasma protein is Factor VIII.

In yet another particularly preferred embodiment of the present invention, the liquid formulation is an aqueous liquid formulation. Preferably, the aqueous liquid formulation contains one or more pH buffering compound to maintain the pH of the formulation at a predetermined level, such as in the range of 5.8 to 6.8. Preferably, the pH buffering compound used in the aqueous liquid formulation is an amino acid or mixture of amino acids; more preferably, the pH buffering compound is histidine or a mixture of amino acids one of which is histidine.

Alternatively, the pH buffering compound is preferably an agent which maintains the pH of the formulation at a predetermined level, such as in the range of 5.8 to 6.8, and which does not chelate calcium ions. Illustrative examples of such pH buffering compounds include, but are not limited to, imidazole and acetate ions.

The pH buffering compound may be present in any amount suitable to maintain the pH of the aqueous liquid formulation at a predetermined level. Preferably, when the pH buffering compound is an amino acid, the concentration of the amino acid is between 0.1 millimole/liter (0.1 mM) and 1000 mM (1 M). More preferably, the concentration of the amino acid is between 5 mM and 100 mM, most preferably between 10 mM and 50 mM.

Preferably, the pH buffering compound maintains the pH of the aqueous formulation at a level of at least 4.0. More preferably, when the plasma protein is Factor IX, the pH buffering compounds maintains the pH at a level between 5.5 and 8.0, even more preferably at a level between 5.5 and 6.8, and most preferably between 5.8 and 6.2.

The inventive aqueous liquid formulation preferably may also contain one or more osmotic modulating agents, i.e., a compound that modulates the osmotic properties (e.g, tonicity, osmolality and/or oncotic pressure) of the formulation to a level that is acceptable to the blood stream and blood cells of recipient individuals. Preferably, the osmotic modulating agent does not chelate calcium ions.

The osmotic modulating agent may be any compound known or available to those skilled in the art that modulates the osmotic properties of the formulation. One skilled in the art may empirically determine the suitability of a given osmotic modulating agent for use in the inventive formulation. Illustrative examples of suitable types of osmotic modulating agents include, but are not limited to: salts, such as sodium chloride and sodium acetate; sugars, such as sucrose and mannitol; amino acids, such as glycine; and mixtures of one or more of these agents and/or types of agents.

The osmotic modulating agent(s) may be present in any concentration sufficient to modulate the osmotic properties of the formulation. Preferably, the osmotic modulating agent (s) may be present in an amount sufficient to modulate the osmolality of the inventive formulation to between 50 and 1000 milliosmoles/L (mOsm/L), more preferably between 100 and 500 mOsm/L, and most preferably between 150 and 350 mOsm/L.

If a salt or combination of salts is employed as the osmotic modulating agent, the total concentration thereof is preferably between 1 mM and 1 M, more preferably between 25 mM and 500 mM, most preferably between 50 mM and 150 mM.

The aqueous liquid formulation preferably further contains a source of multivalent metal ions, such as calcium ions. Any multivalent metal ion that helps stabilize the inventive liquid formulation and that will not adversely affect recipient individuals may be used. Suitable metal ions may be determined empirically by one skilled in the art based on these two criteria and suitable sources of such metal ions are known, and include inorganic and organic salts.

Preferably, the aqueous liquid formulation contains a source of divalent metal ions, such as calcium ions, magnesium ions and/or manganese ions. More preferably, the aqueous liquid formulation contains a source of calcium ions, such as calcium chloride.

The concentration of divalent metal ions, such as calcium ions, in the aqueous liquid formulation is preferably between 0.1 mM and 1 M, more preferably between 2 mM and 200 mM, and most preferably between 10 mM and 100 mM.

In a preferred embodiment of the inventive aqueous liquid formulation, the plasma protein is Factor IX, the pH buffering compound is the amino acid histidine, the osmotic modulating agent is sodium chloride and the source of calcium ions is calcium chloride. Preferably, the concentration of histidine is about 10 mM, the concentration of NaCl is about 100 mM, and the concentration of calcium ions varies with the pH of the formulation. Preferably, when the pH of the aqueous formulation is about 6.2, the concentration of calcium chloride is about 10 mM; when the pH is about 6.0, the concentration of $CaCl_2$ is between 10 mM and 30 mM; and when the pH is about 5.8, the concentration of $CaCl_2$ is between 10 mM and 100 mM.

In another particularly preferred embodiment of the present invention, the liquid formulation is a non-aqueous liquid formulation. Any suitable non-aqueous liquid may be employed in this embodiment of the present invention provided that it provides stability to the plasma protein(s) contained therein. Preferably, the non-aqueous liquid is a hydrophilic liquid. Illustrative examples of suitable non-aqueous liquids include: glycerol; dimethyl sulfoxide (DMSO); polydimethylsiloxane (PMS); ethylene glycols, such as ethylene glycol, diethylene glycol, triethylene glycol, polyethylene glycol ("PEG") 200, PEG 300, and PEG 400; and propylene glycols, such as dipropylene glycol, tripropylene glycol, polypropylene glycol ("PPG") 425, PPG 725, PPG 1000, PPG 2000, PPG 3000 and PPG 4000.

Preferably, the plasma protein is freeze-dried prior to incorporation into the non-aqueous liquid formulation. More preferably, the plasma protein is freeze-dried Factor VIII or freeze-dried Factor IX.

In a highly preferred embodiment of the inventive non-aqueous liquid formulation, the plasma protein is Factor IX and the non-aqueous liquid is an ethylene glycol, such as PEG 200, or a propylene glycol, such as tripropylene glycol, PPG 425, PPG 725, PPG 1000 or PPG 2000. In another highly preferred embodiment of the inventive non-aqueous liquid formulation, the plasma protein is Factor VIII and the non-aqueous liquid is a propylene glycol, such as PPG 425, PPG 725 or PPG 1000.

In another particularly preferred embodiment of the present invention, the liquid formulation is a mixed aqueous/non-aqueous liquid formulation. Any suitable non-aqueous liquid liquid formulation, such as those described above, may be employed in this embodiment of the present invention along with any aqueous liquid formualtion, such as those described above, provided that the mixed aqueous/non-aqueous liquid formulation provides stability to the plasma protein(s) contained therein. Preferably, the non-aqueous liquid in such a formulation is a hydrophilic liquid. Illustrative examples of suitable non-aqueous liquids include: glycerol; DMSO; PMS; ethylene glycols, such as PEG 200, PEG 300, and PEG 400; and propylene-glycols, such as PPG 425, PPG 725, PPG 1000, PPG 2000, PPG 3000 and PPG 4000.

The inventive stable liquid formulation permits storage of one or more plasma proteins in a frozen or an unfrozen liquid state. Preferably, the stable liquid formulation is stored at a temperature of at least −170° C., more preferably at a temperature of at least 0° C., even more preferably at a temperature between 0.1° C. and 42° C., and most preferably between 4° C. and 37° C.

The stable liquid formulation of the present invention maintains at least 50% of the activity of the plasma protein for at least 24 hours in an unfrozen state. Preferably, at least 50% of the activity is maintained for a period of at least 2 days, more preferably at least 30 days, even more preferably at least 180 days, still more preferably at least 540 days, and most preferably at least 3 years.

It will be appreciated that conditions such as hemophilia caused by a decrease in the standard or normal level of activity of one or more plasma proteins in an individual can be treated by administration of one or more of the plasma proteins, such as Factor VIII (for treatment of Hemophilia A) or Factor IX (for treatment of Hemophilia B). Accordingly, a second preferred embodiment of the present invention is directed to a method of treating a patient having a deficiency of one or more plasma proteins which comprises administering to that individual the stable liquid formulation of the present invention.

Continuous administration may be performed according to any of the methods and techniques known to those skilled in the art, including continuous injection or infusion using a surgically implantable pump, such as an Arrow Model 3000 (Arrow International, Walpole, Mass.) or MiniMed 2001 (MiniMed Techologies, Sylmar, Calif.); injection or infusion using an externally worn pump, such as the MiniMed 504S (MiniMed Technologies) or the H-Tron V100 (Disetronic Medical Systems, Minnetonka, Minn.); or diffusion from a biologically-derived bio-resorbable hydrogel, such as a chitosan hydrogel or N,O-carboxymethyl chitosan (NOC-chitosan) hydrogel, alone or in combination with a charged or uncharged polymeic agent to control hydrogel porosity and/or hydrogel stability and/or kinetics of protein relaease, such as polylysine or polypropylene glycol; or diffusion from a synthetically-derived bio-resorbable hydrogel, such as polypropylene glycol, alone or in combination with a charged or uncharged polymeic agent to control hydrogel porosity and/or hydrogel stability and/or kinetics of protein relaease, such as polylysine.

The plasma protein(s) for continuous administration is preferably formulated and dosed in a fashion consistent with good medical practice, taking into account the clinical condition of the individual patient, the site of delivery of the composition, the method of administration, the scheduling of administration, and other factors known to practitioners. The "effective amount" of plasma protein for purposes herein is thus determined by such considerations.

The total pharmaceutically effective amount of plasma protein administered parenterally per dose will preferably be sufficient to provide the plasma protein in a concentration of between about 1 unit/mL to about 2000 units/mL. More preferably, this dose is sufficient to provide a concentration of between about 50 units/mL to about 1500 units/mL, even more preferably between about 100 units/mL to about 1000 units/mL, and most preferably about 600 units/mL. A factor in selecting an appropriate dose is the result obtained, as measured by increases in the level of plasma protein in circulation. The length of treatment needed to observe changes and the interval following treatment for responses to occur may vary depending on the desired effect and the individual being treated.

As a general proposition, the purity of plasma protein formulated according to the present invention will preferably be an appropriate purity known to one of ordinary skill in the relevant art to lead to the optimal stability of the protein. For example, when the plasma protein is Factor IX, the Factor IX is preferably of ultrahigh purity. Preferably, the plasma protein has been subjected to multiple chromatographic purification steps, such as affinity chromatography and preferably immunoaffinity chromatography, to remove substances which cause fragmentation, activation and/or degradation of the plasma protein during manufacture, storage and/or use. Illustrative examples of such substances that are preferably removed by purification include thrombin and Factor IXa; other protein contaminants, such as inter-alpha trypsin inhibitor and pre-alpha trypsin inhibitor; non-protein contaminants, such as lipids; and mixtures of protein and non-protein contaminants, such as lipoproteins.

The concentration of plasma protein(s) employed in the formulations of the present invention is preferably selected to optimize the stability of the plasma protein as may be determined empirically by one skilled in the relevant art. For example, when the plasma protein is Factor IX, the stability of the Factor IX in the inventive formulations is greatest at lower concentrations and tends to decrease as the concentration of Factor IX increases. At Factor IX concentrations below about 100 units/mL (0.4 mg/mL), for example, in one embodiment of the inventive formulations (0.01 M histidine, 0.10 M sodium chloride, 0.01 M calcium chloride, pH 6.8), immunoaffinity-purified Factor IX prepared by the ARC showed no evidence of activation to Factor IXa when incubated at 37° C. for 56 days. At higher Factor IX concentrations (200–600 units/mL), however, the same imunoaffinity-purified Factor IX showed evidence of activation when incubated at 37° C., the extent of activation increasing with increasing protein concentration (FIG. 4). In more acidic embodiments of the inventive formulations, such as pH 5.8–6.2, 600 units/mL (2.4 mg/mL) of the same immunoaffinity-purified Factor IX was incubated with much lower, if any, activation (FIGS. 5 and 8–14).

In a preferred embodiment of the present invention, one or more plasma proteins are contained in a pharmaceutically acceptable carrier. The carrier preferably contains minor amounts of additives such as substances that enhance isotonicity and chemical stability. Such materials are non-toxic to recipients at the dosages and concentrations employed, and include buffers such as phosphate, citrate, succinate, acetate, lactate, tartrate, and other organic acids or their salts; tris-hydroxymethylaminomethane (TRIS), bicarbonate, carbonate, and other organic bases and their salts; antioxidants, such as ascorbic acid; low molecular weight (for example, less than about ten residues) polypeptides, e.g., polyarginine, polylysine, polyglutamate and polyaspartate; proteins, such as serum albumin, gelatin, or immunoglobulins; hydrophilic polymers, such as polyvinylpyrrolidone (PVP), polypropylene glycols (PPGs), and polyethylene glycols (PEGs); amino acids, such as glycine, glutamic acid, aspartic acid, histidine, lysine, or arginine; monosaccharides, disaccharides, and other carbohydrates including cellulose or its derivatives, glucose, mannose, sucrose, dextrins or sulfated carbohydrate derivatives, such as heparin, chondroitin sulfate or dextran sulfate; polyvalent metal ions, such as divalent metal ions including calcium ions, magnesium ions and manganese ions; chelating agents, such as EDTA; sugar alcohols, such as mannitol or sorbitol; counterions, such as sodium or amonium; and/or nonionic surfactants, such as polysorbates or poloxamers.

Such compositions may be administered orally, rectally, parenterally, subcutaneously, intracistemally, intravaginally, intraperitoneally, topically (as by powders, ointments, drops or transdermal patch), bucally, or as an oral or nasal spray, into the lungs or as an inhalant. Preferably, the pharmaceutically acceptable carrier is a biologically-derived bioresorbable hydrogel, such as a chitin hydrogel or chitosan hydrogel.

The plasma protein (or proteins) may also suitably be administered by sustained-release systems. Suitable examples of sustained-release compositions include semipermeable polymer matrices in the form of shaped articles, e.g., films, or microcapsules. Sustained-release matrices include, but are not limited to, polylactides (U.S. Pat. No. 3,773,919; European Patent No. 58,481), copolymers of L-glutamic acid and gamma-ethyl-L-glutamate (U. Sidman et al., *Biopolymers* 22:547–556 (1983)), poly (2-hydroxyethyl methacrylate) or ethylene vinyl acetate (R. Langer et al., *J Biomed. Mater. Res.* 15:167–277 (1981); R. Langer, *Chem. Tech.* 12:98–105 (1982)), or poly-D-(–)-3-hydroxybutyric acid (European Patent No. 133,988). Sustained-release plasma protein compositions also include liposomally entrapped plasma proteins. Liposomes containing one or more plasma proteins may be prepared by any of the methods known to those skilled in the art, for example, as described in DE 3,218,121; Epstein et al., *Proc. Natl. Acad. Sci.* (USA) 82:3688–3692 (1985); Hwang et al., *Proc. Natl. Acad. Sci.* (USA) 77:4030–4034 (1980); EP 52,322; EP 36,676; EP 88,046; EP 143,949; EP 142,641; Japanese Pat. Appl. 83-118008; U.S. Pat. Nos. 4,485,045 and 4,544,545; and EP 102,324. Ordinarily, the liposomes are of the small (about 200–800 Angstroms) unilamellar type in which the lipid content is greater than about 30 mol. percent cholesterol, the selected proportion being adjusted for the optimal therapy.

Compositions containing one or more plasma proteins to be used for therapeutic administration must be sterile. Sterility is readily accomplished by filtration through sterile filtration membranes (e.g., 0.2 micron membranes), by gamma irradiation, or any other suitable means known to those skilled in the art. Therapeutic polypeptide compositions generally are placed into a container having a sterile access port, for example, an intravenous solution bag or vial having a stopper pierceable by a hypodermic injection needle.

These compositions ordinarily will be stored in unit or multi-dose containers, for example, sealed ampules or vials, as an aqueous solution or as a lyophilized formulation for reconstitution. As an example of a lyophilized formulation, 10 mL vials are filled with 5 mL of sterile-filtered 1% (w/v) aqueous plasma protein solution, such as an aqueous solution of Factor IX or Factor VIII, and the resulting mixture is lyophilized. The infusion solution is prepared by reconstituting the lyophilized material using sterile Water-for-Injection (WFI).

The present invention further provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the pharmaceutical compositions of the present invention may be employed in conjunction with other therapeutic compounds.

A preferred embodiment of the present invention provides a plasma protein in a stable liquid as part of a kit. A more preferred embodiment provides a plasma protein in a stable liquid in a kit whereby the kit provides for the delivery of the plasma protein by injection. A yet more preferred embodiment provides a plasma protein in a stable liquid in a kit whereby the kit provides for injection by and includes but is not limited to a syringe and/or needle. A still more preferred embodiment provides a plasma protein in a stable liquid in a kit whereby the kit provides for the injection of the liquid into a reservoir of a continuous injection or infusion system for intravenous, subcutaneous, intradermal, intramuscular, intraperitoneal, or intranasal delivery.

Another still more preferred embodiment provides a plasma protein in a stable liquid in a kit whereby the kit provides for the incorporation of the liquid into a hydrogel and the subsequent introduction of the plasma protein-containing hydrogel by injection, such as subcutaneous, intradermal, intramuscular, intraperitoneal, and the like; by topical application for transdermal, intranasal, by buccal absorption through skin surfaces, mucous membranes, and the like; or by inhalation into the nose and/or lungs. Yet another more preferred embodiment provides for the delivery of a plasma protein in a stable liquid in microspheres or hydrogel for injection or implantation, including but not limited to injection, such as subcutaneous, intradermal, intramuscular, intraperitoneal, and the like.

The various embodiments of the present invention have several advantages over previously used compositions and methods.

A first advantage is that the plasma protein formulation of the present invention is ready to use without on-site preparation. This enables delivery of the protein sooner than those lyophilized formulations that require rehydration.

A second advantage is that the present invention enhances stability of the plasma protein in solution. The formulation of the present invention allows storage of the protein in liquid for longer periods at a given level of activity than is possible with rehydrated previously used formulations. This stability is enhanced during storage under refrigeration and at body temperature. Stability at body temperature enables the plasma protein to be held in a reservoir either subcutaneously or on the body surface in a continuous injection or infusion delivery system. It also permits delivery by diffusion from a supplemented hydrogel whereby the composition of the present invention is incorporated into the hydrogel prior to injection or infusion.

A third advantage of the present invention is the ability to store the plasma protein without the additional cost and restriction of refrigeration. While the present invention demonstrates as an example extended storage of Factor IX under refrigeration, 4° C., for over one year without loss of activity, it also demonstrates storage at body temperature, 37° C., for over one month. For situations where refrigeration is not possible, the present invention permits the storage of ready-to-inject plasma proteins at room temperature, for use either prophylactically or in emergency situations.

A fourth advantage of the present invention is the ability to prophylactically treat congenital or acquired plasma protein deficiency in a manner that provides a continuous level of the plasma protein that more closely resembles the level found in normal plasma and achieves normal hemostasis. It is the uninterrupted condition of normal hemostasis that prevents the progressive, cumulative, unrepairable tissue damage that permanently debilitates patients. The elimination of the risk of bleeding episodes and their consequent damage also significantly enhances the quality of life for the patients and their families, enabling younger patients to more fully participate in activities normal for young children, and for older patients to hold jobs and contribute to society.

The following examples are illustrative only and are not intended to limit the scope of the invention as defined by the appended claims. It will be apparent to those skilled in the art that various modifications and variations can be made in the methods of the present invention without departing from the spirit and scope of the invention. Thus, it is intended that the present invention cover the modifications and variations of this invention provided they come within the scope of the appended claims and their equivalents.

All patents and publications referred to herein are expressly incorporated by reference.

VI. EXAMPLES

A. Materials

Coagulation Factor IX, Heat Treated (CFIX-HT): Intermediate-purity Factor IX concentrate prepared from pooled human plasma by anion-exchange chromatography, to capture vitamin K-dependent clotting factors, followed by sulfated-dextran chromatography, to separate these factors; freeze dried and dry-heat treated to reduce viral infectivity. Manufactured for ARC by Baxter/Hyland, Glendale Calif. Product consists of 10–20% Factor IX, very small amounts of Factors II and X. The bulk of the protein (70–80%) is Inter-alpha Trypsin Inhibitor (IaI).

Coagulation Factor IX, Solvent and Detergent Treated (CFIX-SD): Intermediate-purity Factor IX concentrate prepared by the same chromatographic steps as CFIX-HT, but treated with Tri-n-butyl phosphate (TNBP) and Triton X-100 to inactivate viruses prior to the final chromatography step. Otherwise similar to CFIX-HT.

Factor IX-M (Hyland): An ultra high-purity concentrate prepared from pooled human plasma in pilot scale manufacturing at the Baxter/Hyland plant in Glendale Calif. Process utilizes anion-exchange chromatography, solvent/detergent treatment, immunoaffinity chromatography on a 7.5 liter column of immobilized metal-ion dependent anti-human Factor IX monoclonal antibody (anti-FIX-Mab), and a final anion-exchange polishing step.

Factor IX-M (JHL): An ultra-high purity concentrate prepared at the ARC Jerome Holland Laboratory in Rockville MD. CFIX-SD was reconstituted, applied to a one liter of anti-FIX Mab resin in the presence of 40 mM MgCl$_2$, washed with 1 M NaCl/10 mM MgCl$_2$, and eluted with citrate/NaCl buffer. Preparations designated "w/DEAE" were further purified on an anion-exchange column to diminish levels of mouse IgG and other contaminants. Specific activity and SD S-PAGE indicate the purity of all FIX-M preps was greater than or equal to 95%.

Alphanine (ARC/A9): High-purity Factor IX concentrate prepared for ARC, from a DEAE eluate from pooled human ARC plasma, by Alpha Pharmaceuticals according to their proprietary purification method by subjecting this eluate to barium citrate adsorption, solvent/detergent treatment and two affinity chromatographic steps on dextran sulfate agarose; provided lyophilized in Alpha proprietary formulation. Dialyzed into ARC formulation for stability testing.

Mononine (ARC/M9): High-purity Factor IX concentrate is manufactured by Armour Pharmaceuticals by a method including immunoaffinity chromatography on an immobilized monoclonal antibody to Factor IX, followed by chromatography on hexylamine agarose.

B. Example 1

Effect of Buffer, Divalent Cations, and Other Excipients on the Stability of Coagulation Factor IX CFIX-M (JHL)/DEAE was dialyzed into 0.01 M histidine, 0.1 M NaCl, pH 6.8 (histidine-saline) or was left in 0.02 M sodium citrate (NaCit), 0.11 NaCl, pH 6.8 (citrate-saline). An aliquot of the solution was mixed with an equal volume of 2X additive, prepared at twice the desired final concentration in the appropriate buffer (histidine-saline or citrate-saline). The formulated solutions were sterile filtered, aseptically dispensed into sterilized tubes, incubated at 37° C. or 4° C. for the designated length of time, and frozen until the end of the study, when the samples were thawed and assayed.

Factor IX coagulation assays were performed by a one-stage method using Kontakt brand APTT (Pacific Haemostasis) and congenital Factor IX-deficient plasma (George King or Universal Reagents). The standard was a lyophilized CFIX-SD concentrate. Working dilutions of Factor IX were prepared in 0.05 M imidazole buffer, pH 7.3, containing 0.1 M NaCl, 0.1% bovine serum albumin (BSA), and 0.01% Tween 20 to protect the protein from loss and denaturation at surfaces. The samples were assayed on an MLA Electra 900 Automatic Coagulation Timer. Two or more standard curves were included for all runs.

In vitro half-lives ($T_{1/2}$), the time in days at which Factor IX clotting activity declined to 50% of the original activity, were determined from straight-line semi-log plots of the log of the % of initial activity remaining versus days of incubation.

RESULTS

The stability of samples is shown in Table 1, below:

TABLE 1

In Vitro Half-life ($T_{1/2}$ in Days) of Factor IX Clotting Activity (100 Units/ml) at pH 6.8

| NO. | FORMULATION | $T_{1/2}$, 37° C. | $T_{1/2}$, 4° C. |
|---|---|---|---|
| 1 | 0.01M Hist/0.1M NaCl | 12.0 | 310 |
| 2 | 0.01M Hist/0.1M NaCl + 10 mM CaCl$_2$ | 41 | 540 |
| 3 | 0.01M Hist/0.1M NaCl + 10 mM MgCl$_2$ | 10 | 305 |
| 4 | 0.02M NaCit/0.11M NaCl | 10.0 | 110 |
| 5 | 0.02M NaCit/0.11M NaCl + 40 mM CaCl$_2$ | 5 | 300 |
| 6 | 0.01M Hist/0.1M NaCl + Heparin, 2 u/mL | 8 | — |
| 7 | 0.01M Hist/0.1M NaCl + Heparin, 2 u/ml + 10 mM CaCl$_2$ | 36 | — |
| 8 | 0.01M Hist/0.1M NaCl + 1 mM Choline | 9 | — |

Factor IX-M (JHL) w/DEAE polishing column

The indications of Example 1 are:

(1) Histidine provides greater stability than citrate, especially at 4° C. (No. 1 vs No. 4).

(2) Calcium cannot be replaced by magnesium (No. 3 vs. No. 2).

(3) The presence of heparin does not improve Factor IX stability (No. 6, No. 7).

C. Example 2

Effect of Various Excipients on Stability of Coagulation Factor IX in Histidine-Saline CFIX-M (JHL) in citrate-saline was diluted 1:10 in 0.01 M histidine, 0.1 M NaCl, pH 6.8 (histidine-saline) to give a final composition of 0.009 M histidine, 0.002 M citrate, 0.1 M NaCl, pH 6.8 (Buffer A) or was dialyzed against histidine-saline (Buffer B). Thereafter, the samples were treated as in Example 1, above, with the following changes:

(1) Samples were incubated at 37° C., as indicated on the table below.
(2) Factor IX coagulation assays were performed on a Lancer Coagulyzer II.

RESULTS

The stability of samples is shown in Table 2, below:

TABLE 2

In Vitro Half-life ($T_{1/2}$ in Days) of Clotting Activity of Factor IX-M at 37° C.

| NUMBER | FORMULATION | $T_{1/2}$ (DAYS) |
|---|---|---|
| 1 | 0.009M Histidine, 0.002M citrate, 0.1M NaCl, pH 6.0 | 2.2 |
| 2 | 0.009M Histidine, 0.002M citrate, 0.1M NaCl, pH 8.0 | 4.2 |
| 3 | 0.009M Histidine, 0.002M citrate, 0.1M NaCl, pH 6.8 (Buffer A) | 5.0 |
| 4 | 0.05M Glycine in Buffer A | 2.8 |
| 5 | 0.5M Glycine in Buffer A | 3.0 |
| 6 | 0.1% PEG 4000 in Buffer A | 4.0 |
| 7 | 1.0% PEG 4000 in Buffer A | 5.0 |
| 8 | 0.1% Albumin (BSA) in Buffer A | 1.3 |
| 9 | 1.0% Albumin (BSA) in Buffer A | 1.8 |
| 10 | 0.01% Tween in Buffer A | 3.0 |
| 11 | 0.10% Tween in Buffer A | 5.0 |
| 12 | 0.01M Histidine, 0.1M NaCl, pH 6.8 (Buffer B) | 5.0 |
| 13 | 0.1M Glycine, 2.5 mM $CaCl_2$ in Buffer B | 28.0 |
| 14 | 5 mM $CaCl_2$ in Buffer B | 30.0 |
| 15 | 100 mM $CaCl_2$ in Buffer B | 30.0 |

Factor IX-M (JHL) w/o DEAE polishing column

The initial indications are:

(1) The absence of calcium may inhibit the stability of the Factor IX.
(2) Addition of the other tested excipients—glycine, polyethylene glycol (PEG), albumin or Tween—cannot compensate for an absence of calcium.
(3) Factor IX is destabilized by albumin.

D. Example 3

Effect of pH, Purity and Excipients on Stability of Coagulation Factor IX

Factor IX-M (JHL) with or without DEAE polishing, CFIX-SD, and Alphanine in ARC formulation (ARC/A9) were treated as in Example 2, above.

RESULTS

The stability of samples is shown in Table 3, below:

TABLE 3

In Vitro Half-life ($T_{1/2}$ in Days) of Clotting Activity of Factor IX at 37° C.

| NO. | FORMULATION | pH | FIX | $T_{1/2}$, 37° C. |
|---|---|---|---|---|
| 1 | 0.01M Hist/0.1M NaCl + 10 mM $CaCl_2$ | 6.8 | DEAE | 49 |
| 2 | 0.01M Hist/0.1M NaCl | 6.8 | DEAE | 12 |
| 3 | Hist/NaCl + 20% Sucrose + 10 mM $CaCl_2$ | 6.8 | DEAE | 42 |
| 4 | Hist/NaCl + 0.5M Glycine + 20% Sucrose + 10 mM $CaCl_2$ | 6.8 | DEAE | 37 |
| 5 | Hist/NaCl + 10 mM CaCl | 6.8 | CFIX-SD | 18* |
| 6 | Hist/NaCl | 6.9 | CFIX-SD | 7 |
| 7 | Hist/NaCl + 10 mM $CaCl_2$ | 6.8 | ARC/A9 | 17 |
| 8 | Hist/NaCl | 6.9 | ARC/A9 | 2.5 |
| 9 | Hist/NaCl + 10 mM $CaCl_2$ | 6.0 | DEAE | 43 |
| 10 | Hist/NaCl + 10 mM $CaCl_2$ | 6.8 | DEAE | 43 |
| 11 | Hist/NaCl + 10 mM $CaCl_2$ | 7.4 | DEAE | 35 |
| 12 | Hist/NaCl + 10 mM $CaCl_2$ | 8.0 | DEAE | 16 |
| 13 | Hist/NaCl + 0.5M Lysine + 10 mM $CaCl_2$ + 20% Sucrose | 6.8 | DEAE | 6 |
| 14 | 0.01M Hist/0.1M NaCl | 6.8 | FIX-M | 8 |

FIX-M = Factor IX-M (JHL) w/o DEAE polishing column
DEAE Factor IX-M (JHL) w/DEAE polishing column
ARC/A9 = ARC Alphanine-SD
CFIX-SD = ARC CFIX-SD The data of Table 3 are graphed in FIG. 2.

The indications of Example 3 are:

(1) Factor IX is destabilized by impurities: CFIX-SD has much lower stability with and without $CaCl_2$ than FIX-M/DEAE (Nos. 5, 6 vs. Nos. 1, 2); ARC/A9 has much lower stability with and without $CaCl_2$ than FIX-M/DEAE (Nos. 7, 8 vs. Nos. 1, 2); FIX-M without DEAE polishing has lower stability than with DEAE polishing (No. 14 vs. No. 2).
(2) Factor IX is destabilized by lysine and glycine.
(3) The buffer cited by Octapharma (See No. 13, WO 91-10439) does not provide the stability of the present invention (No. 13).
(4) The range of pH that provides the greatest stability of Factor IX is 6.0 to 6.8.

E. Example 4

Stability of Coagulation Factor IX in Non-aqueous Liquid Formulations

CFIX-M (JHL) is formulated as a lyophilized mixture of the following components:

(1) 38 milligrams (mg) Coagulation Factor IX
(2) 70 mg NaCl
(3) 290 mg glycine
(4) 8.8 mg $CaCl_2$
(5) 6 mg histidine.

Aliquots (100 mg) of this dry mixture were resuspended and/or dissolved by syringe in 900–1000 microliters of one of the solvents (polypropylene glycol (molecular weight 425)(PPG); poly(dimethyl siloxane)(PMS); glycerol; or water). These were then aliquoted as 100 microliter samples into ten vials, sealed, and incubated at 37° C. Factor IX coagulation assays were performed as described in Example 1.

RESULTS

The stability of samples is shown in Table 4 below:

TABLE 4

In Vitro Stability of Factor IX in Non-Aqueous Liquid Formulations

| SOLVENT | HALF LIFE (Days) | FINAL ACTIVITY (% original) AT 14 DAYS |
|---|---|---|
| PMS | 5.5 | 23 |
| PPG | 14 | 50 |
| Glycerol | 11 | 36 |
| Water | 12 | 29 |

The data of Table 4 are graphed in FIG. 6.
The results indicate:
(1) PPG provided the greatest stability for Coagulation Factor IX.
(2) PMS provided the least stability for Coagulation Factor IX.

F. Example 5

Stability of Coagulation Factor VIII in Non-aqueous Liquid Formulations

Coagulation Factor VIII (Baxter AHFM) is provided as a lyophilized mixture that provides a final composition in 7.5 mL of:
(1) 1000–1200 units Coagulation Factor VIII (133–160 units/mL)
(2) Human Albumin, 16.7 mg/mL
(3) Polyethylene glycol, 2.0 mg/mL
(4) 73 millimoles/liter Histidine
(5) 40 millimoles/liter Glycine.

A 100 mg aliquot of this powder was resuspended and/or dissolved in 2.5 mL of solvent (polypropylene glycol (molecular weight 425)(PPG); polyethylene glycol (molecular weight 300)(PEG); or water) by syringe-to-syringe mixing and distributed into 100 microliter aliquots. These vials were then incubated at 37° C.

Factor VIII activity assays were performed according to the method used in Example I for Factor IX, but using Mega I (Office of Biologics Research and Review, Bethesda Md.) as a Factor VIII standard in place of the Factor IX standard, and using Factor VIII-depleted plasma (Universal Reagents) in place of the Factor IX-deficient plasma.

RESULTS

The stability of samples is shown in Table 5, below:

TABLE 5

In Vitro Stability of Factor VIII in Non-Aqueous Liquid Formulations

| SOLVENT | HALF LIFE (Days) | FINAL ACTIVITY (% original) |
|---|---|---|
| PPG | 23 | 44 |
| PEG | 3 | 0 |
| Water | 18 | 29 |

The data of Table 5 is graphed in FIG. 7.

The results indicate that both PPG and water demonstrated an activity spike at 7 days, with a marked decrease following. PEG as a solvent resulted in an almost immediate inactivation of Factor VIII, without the activity spike preceding.

This Example, and Example 4 above with Factor IX in non-aqueous liquid formulations, may be considered preliminary experiments to tst the concept of using non-aqueous solvents for clotting factor stabilization. The spike in activity at day 7 with Factor VIII in PPG and water, and with Factor IX in PPG, may be due to activation caused by bacterial contamination of the materials during syringe-to-syringe mixing. The experimental technique was modified and improved in subsequent experiments with non-aqueous liquid formulations, described in Example 8 (Table 7, FIGS. 16 and 17) and Example 9 below (FIGS. 18 and 19).

G. Example 6

Optimization of Aqueous Formulations for Factor IX at 37° C.

For optimization of pH and calcium concentration, highly purified Factor IX-M with DEA polishing was prepared at a relatively high concentration (2.4 mg/mL; 600 units/mL), a condition under which the protein tends to be activated and fragmented during extended incubation at 37° C. The formulations contained 10 mM histidine, 0.1 M sodium chloride and calcium chloride at one of the following concentrations: 10 mM, 30 mM and 100 mM. Each formulation was adjusted to one of the following pH values: 5.8, 6.0 and 6.2. The formulations were sterile filtered, dispensed aseptically into autoclaved polypropylene tubes and incubated at 37° C.

Samples of each formulation were removed at weekly intervals and frozen at −80° C. After 56 days, all samples were thawed and analyzed for Factor IX clotting activity by a one-stage APTT coagulation assay with a substrate of Factor IX-deficient plasma. Percent activity was plotted versus days of incubation and the in vitro half-life ($T_{1/2}$) was determined as the time in days at which the curve crossed the 50% activity line.

RESULTS

Decay curves of % initial clotting activity are shown in FIGS. 8–10. When results at each of the three pH values were plotted for 10 mM $CaCl_2$ (FIG. 8), the half-life of clotting activity varied from 38 days to 58 days, with a slightly biphasic curve (having an initial steady decrease for several weeks followed by a gently rising curve or change in slope) suggestive of possible activation at pH 6.2. Similarly, at 30 mM $CaCl_2$, clear evidence of activation appeared in the pH 6.2 samples (FIG. 9). At 100 mM $CaCl_2$, there is a slight indication of possible activation at pH 6.0 and pH 6.2 after 40 days (FIG. 10). Table 6 below summarizes the half-life values, and indicates where activation appears possible or likely based on the slight biphasic nature of the decay curves. It appears from this summary that pH 5.8 is superior to pH 6.0 or pH6.2.

In FIGS. 11, 12 and 13, the three $CaCl_2$ concentrations are compared at each pH value. The shallower decay curves seen at 100 mM $CaCl_2$ at both pH 6.0 and pH 6.2 may reflect Factor IX activation. This highest $CaCl_2$ concentration may be detrimental to long-term stability. In addition, there was clear evidence of activation at 30 mM $CaCl_2$ at pH 6.2, and this condition may also be suboptimal.

SDS-PAGE gels with Coomassie Blue staining for the nine pH/$CaCl_2$ combinations incubated at 37° C. are shown in FIG. 14A for days 0 and 56 and FIGS. 14B, 14C and 14D (reduced gels) for all time points. Gels were run in reduced and non-reduced condition (with or without 2-mercaptoethanol added to dissolve disulfide bonds holding fragments together). At zero time, Factor IX looked the same in all formulations, except that in 100 mM $CaCl_2$ there was high molecular weight smearing in the reduced gels (probably due to non-specific salt effects). High molecular weight smearing was not seen when the 100 mM $CaCl_2$ samples were diluted with water (FIG. 14D). At 56 days, there was fragmentation in all samples, but clear differences between samples were evident in the reduced gel in FIG. 14A. The best conditions with least fragmentation and the greatest amount of intact monomer appeared in lanes 6–7 (30 mM Ca at pH 5.8–6.0) and lanes 9–10 (100 mM Ca at pH 5.8–6.0). The time studies in FIGS. 14B–14D confirm that the least amount of fragmentation was observed at pH 5.8–6.0 at 30 mM Ca or greater.

Based on the clotting activity, the best $CaCl_2$ concentration appears to be 30–100 mM. At pH 5.8 and 6.0, however, the stability of Factor IX ($T_{1/2}$) increased with increasing $CaCl_2$ concentration. The shallower curves observed at higher $CaCl_2$ concentrations proabably indicate improved stability rather than Factor IX activation; SDS-PAGE data suggest that $CaCl_2$ concentrations of $\geq 30$ mM are best at pH 5.8 or 6.0. Previous results (data not shown) indicate that the stability of Factor IX is very short at pH 5.5.

TABLE 6

Factor IX Clotting Activity $T_{1/2}$ Values and Possible Activation upon Incubation of High-Purity Factor IX (600 units/mL) at 37° C. in Liquid Formulation Containing 10–100 mM $CaCl_2$ at pH 5.8–6.2

| FORMULATION OF 10 mM HISTIDINE, | CLOTTING ACTIVITY HALF-LIFE | | |
|---|---|---|---|
| 0.1M NaCl PLUS | pH 5.8 | pH 6.0 | pH 6.2 |
| 10 mM $CaCl_2$ | 47 | 38 | 58 (activated?) |
| 30 mM $CaCl_2$ | 52 | 56 | ? (activated?) |
| 100 mM $CaCl_2$ | 57 | >60 (activated?) | >60 (activated?) |

H. Example 7

Evaluation of Aqueous Factor IX Formulations at 4° C.

Formulation handling and assays were performed as in Example 6. Six formulations containing various concentrations of Factor IX (25 units/mL–600 units/mL) were prepared with 10 mM histidine, 0.1 M NaCl, 10 mM $CaCl_2$, pH 6.8. Samples of each formulation were incubated in a cold room (4° C.), frozen and assayed for clotting activity.

RESULTS

FIG. 15 shows the decay curves for samples incubated at 4° C. Elevation of clotting activity above the initial 100% activity, indicative of Factor IX activation, is evident at 600 units/mL (70 days), 300 units/mL (140 days), 200 units/mL (210 days) and 100 units/mL (410 days). No evidence of activation was detected at 20 units/mL or 50 units/mL up to 410 days. At the 410 day time point, more than 80% of the initial activity remained in these samples.

I. Example 8

Non-aqueous Formulations for Factor VIII

The freeze-dried Factor VIII used in this Example was Antihemophilic Factor, Human, Method M, Solvent and Detergent Treated (AHF-M) prepared from American Red Cross donor plasma by Baxter Healthcare Hyland Division (Glendale, Calif.). For each experiment, a vial of AHF-M (approximately 1000 units) was suspended in 10 mL of a non-aqueous solvents by adding the solvent aseptically with a hypodermic needle to the freeze-dried Factor VIII powder in an unopened vial, and alowing the suspension to liquify. Among the solvents tested were: glycerol, dimethyl sulfoxide (DMSO), ethylene glycol, diethylene glycol, triethylene glycol, polyethylene glycol (PEG) 200, PEG 300, PEG 400, dipropylene glycol, tripropylene glycol, polypropylene glycol (PPG) 425, PPG 725, PPG 1000, PPG 2000, PPG 3000 and PPG 4000. Each suspension was aseptically aliquoted into sterilized polypropylene tubes. The tubes were incubated at 37° C., removed at various times, diluted and assayed for clotting activity.

RESULTS

In some non-aqueous solvents (glycerol, DMSO, ethylene glycol), Factor VIII activity appeared to be rapidly inactivated based on undetectable activity levels even in unincubated zero time controls (Table 7). These solvents were not found to inhibit the clotting assay when diluted to the concentrations present in diluted Factor VIII samples.

The clotting activity of Factor VIII in dipropylene glycol, tripropylene glycol and polyethylene glycol was also lost quickly; half-life values in these solvents were four days or less.

In contrast, in PPG 425, PPG 725and PPG 1000, Factor VIII activity was maintained as well as, or better than, the activity of Factor VIII dissolved in water (FIG. 16; Table 7). While the half-life of Factor VIII in aqueous solution was 34 days, the half-life was 42 days in PPG 425, $\geq 60$ days in PPG 725, and $\geq 90$ days in PPG 1000.

When plotted against PPG oligomer size (i.e. the number of monomer units found in the PPG polymer), half-life values for Factor VIII clotting activity are nearly linear with oligomer size up to about PPG 1000, an oligomer of 17 monomer units (FIG. 17). Larger PPG polymers (PPG 2000 and PPG 3000) also gave high stability, but the viscosity of these polymers caused variations due to difficulty in obtaining accurate sample volumes. PPG 4000 appeared to give lower stability.

PEG was ineffective in stabilizing Factor VIII up to PEG 400 (oligomer size=4 monomer units) (FIG. 16; Table 7). Higher oligomers of PEG were solid at room temperature and so were not further evaluated.

TABLE 7

In Vitro Half-life ($T_{1/2}$ in Days) of Freeze-Dried Factor VIII (AHF-M) Suspended in Non-Aqueous Liquid Formulations at 37° C.

| NUMBER | SOLVENT | $T_{1/2}$ (DAYS) |
|---|---|---|
| 1 | Water | 34 |
| 2 | DMSO | 0 |
| 3 | Glycerol | 0 |
| 4 | PPG 134 (Dipropylene Glycol) | 3 |
| 5 | PPG 192 (Tripropylene Glycol) | 4 |
| 6 | PPG 425 (7-mer) | 42 |
| 7 | PPG 725 (12-mer) | $\geq 60$ |
| 8 | PPG 1000 (17-mer) | $\geq 90$ |
| 9 | PEG 150 (Triethylene Glycol) | 0 |
| 10 | PEG 200 (Tetraethylene Glycol) | 2 |
| 11 | PEG 300 (7-mer) | ~3 |
| 12 | PEG 400 (9-mer) | ~3 |

J. Example 9

Non-aqueous Formulations for Factor IX

Immunoaffinity-purified Factor IX was freeze-dried in 2.5 mL volumes in a Virtis freeze-dryer. For each experiment, 7 mg of dried Factor IX was suspended in 10 mL of non-aqueous solvent. The solvents tested were: PEG 200, PEG 300, PEG 400, tripropylene glycol, PPG 425, PPG 725, PPG 1000, PPG 2000, PPG 3000 and PPG 4000. Each suspension was aseptically aliquoted into sterilized polypropylene tubes that were incubated at 37° C. for various times, removed, diluted and assayed for clotting activity.

In contrast to the results obtained with Factor VIII in Example 8, polyethylene glycols offered some stability to Factor IX, as shown in FIG. 18. While PEG 300 and PEG 400 each gave a half-life value of under 5 days, the half-life with PEG 200 (tetraethylene glycol) was 17 days (which is less than half the $T_{1/2}$ in aqueous solution).

Polypropylene glycols stabilized Factor IX to a significant extent. In tripropylene glycol, the half-life was about 56 days, compared with 39 days in aqueous solution. In PPG 425, PPG 725, PPG 1000 and PPG 2000, the half-life was not reached after 56 days (FIG. 19; irregularities were probably due to sampling errors).

K. Example 10

In Vitro Delivery of Clotting Factors with Implantable Pumps

Two Arrow Model 3000 pumps (Arrow International, Walpole, Mass.) were used, which have a reservoir volume of 30 mL and a delivery rate of 2 mL/day. These pumps are licensed in the United States for implantation in the abdominal area, with intrathecal or hepatic artery access.

Aqueous solutions of Factor VIII (AHF-M) and Factor IX were injected into the pump septum/port according to the standard protocol for filling the pump. Each pump was placed in a water bath at 37° C. to activate the pumping mechanism, and the contents were delivered through an internal sterile filter via an exit catheter into a collection tube. Samples were collected daily for 13 days and the volume and clotting activity were measured.

RESULTS

Effluent volume was maintained accurately at 2 mL/day for both pumps (FIGS. 20 and 21).

Factor VIII activity was 95% lost by day 6 (FIG. 20). This was determined to be caused, however, by bacterial contamination when sterility was compromised during the process of filling the pump with AHF-M solution (bacterial contamination was confirmed by agar plate colony and culture assessment).

Factor IX activity in the effluent from the pump decreased relatively steadily throughout the 13 days of operation (FIG. 21). The half-life was 18–20 days, about half that observed in polypropylene tubes, At day 13, the effluent activity was 60% of the starting activity. The units of Factor IX delivered per day was 185–210 units for the first five days, decreasing to 160–170 units during days 6–11 and decreasing further to 110–140 units for the final two days (FIG. 22). No bacteria were detected in the Factor IX effluent.

L. Example 11

Biocompatibility/delivery of Factor VIII with Implantable Pump

Two Arrow Model 3000 pumps (Arrow International, Walpole, Mass.) with delivery rates of 1 mL/day were filled aseptically with a sterile aqueous solution of Factor VIII (reconstituted AHF-M, Lot No. 29355011AA; 80 Factor VIII clotting units/mL). One pump was placed in a 37° C. water bath to activate the pumping mechanism, and the contents were delivered via a 0.2 micron filter, glass flow constrictor and silicone rubber exit catheter into a collection tube as described in Example 10. Effluent samples were collected every one to four days and clotting activity was measured by one-stage APTT assay.

To determine the biocompatibility of Factor VIII with the titanium pump reservoir, the exit catheter of the second filled pump was tied in a knot to prevent solution outflow and maintain the entire 30 mL of Factor VIII solution in the reservoir. Samples were withdrawn aseptically from the reservoir with a sterile hypodermic syringe needle every one to four days, and Factor VIII clotting activity was measured as described above.

RESULTS

The activity of Factor VIII samples which were allowed to flow from the pump and those taken from the pump reservoir under stasis did not differ significantly (FIG. 23). The dip in the first samples of pump effluent was due to dilution of the effluent with the saline solution used to purge the pump tubing.

When the decay curve for Factor VIII sampled from the titanium pump reservoir under static conditions was compared to the decay curve for Factor VIII incubated in polypropylene tubes in an earlier experiment, the decay was more rapid in the pump than in the polypropylene tubes (FIG. 24). The in vitro half-life in the titanium reservoir was approximately 22 days, compared to a half-life of about 38 days in polypropylene tubes. This faster decay in the pump reservoir may reflect increased binding, denaturation or fragmentation of Factor VIII in the presence of the titanium surface of the reservoir under the conditions used for testing. Alternatively, the polypropylene surface of the tubes may, in fact, stabilize Factor VIII by some unknown mechanism.

The lower observed stability of Factor VIII incubated at 37° C. in the titanium reservoir of the Arrow Model 3000 pump compared to the observed stability of Factor VIII incubated at 37° C. in polypropylene tubes suggests a difference in the biocompatibility of these two materials with Factor VIII. No difference was observed, however, in the stability of Factor VIII incubated statically inside the pump reservoir and Factor VIII pumped out through the glass/silicone rubber exit catheter. This suggests that the glass and rubber surfaces do not alter the activity of the Factor VIII exiting the pump.

M. Example 12

Biocompatibility/delivery of Factor IX with Implantable Pump

As in Example 11, two Arrow Model 3000 pumps (Arrow International, Walpole, Mass.) with delivery rates of 1 mL/day were filled aseptically with a sterile-filtered aqueous solution of immunity-purified Factor IX (100 Factor IX clotting units/mL) in 10 mM histidine, 0.10 M NaCl, 10 mM $CaCl_2$, pH 6.2. One pump was placed in a 37° C. water bath to activate the pumping mechanism, and the contents were delivered via a 0.2 micron filter, glass flow constrictor and silicone rubber exit catheter into a collection tube as described above. Effluent samples were collected every one to two and Factor IX clotting activity was measured by one-stage APTT assay.

To determine the biocompatibility of Factor IX with the titanium pump reservoir, the exit catheter of the second filled pump was tied in a knot to prevent solution outflow and maintain the entire 30 mL of Factor IX solution in the reservoir. Samples were withdrawn aseptically from the reservoir with a sterile hypodermic syringe needle every one to two days, and Factor VIII clotting activity was measured as described above.

RESULTS

The activity of Factor IX samples which were allowed to flow from the pump and those taken from the pump reservoir under stasis did not differ significantly (FIG. 25). Both decay curves extrapolate to half-life values of about 25 days.

When the decay curve for Factor IX sampled from the titanium pump reservoir under static conditions was compared to the decay curve for Factor IX incubated in polypropylene tubes in an earlier experiment, the in vitro half-life in the titanium reservoir was approximately 25 days, compared to a half-life of about 35 days in polypropylene tubes (FIG. 26). Although the half-life in the titanium reservoir is shorter, the rate of decay appears to be similar in both the titanium reservoir and polypropylene tubes (i.e. the slopes of the decay curves are roughly equal). The lower half-life of Factor IX in the titanium reservoir appears to be due to an initial drop (about 25%) in Factor IX activity at the time of the first assay (day 2), suggesting that a portion of the Factor IX is bound to the inner surface of the pump reservoir but the remainder is unaffected.

As with Factor VIII, no difference was observed between Factor IX held statically inside the pump reservoir and Factor IX pumped out through the glass/silicone rubber exit catheter, indicating that glass and silicone rubber do not alter the potency of the Factor IX exiting the pump. The half-life of Factor IX incubated at 37° C. in the titanium pump reservoir was lower than that of Factor IX incubated at 37° C. in polypropylene tubes, but this appeared to be due to an initial drop in Factor IX content in the pump reservoir, followed by a rate of decay that was about the same for both materials.

What is claimed is:

1. A stable aqueous liquid formulation of a plasma protein comprising: (a) a plasma protein; (b) a pH buffering compound; (c) a source of calcium ions; (d) an osmotic modulating agent in a concentration of 1–500 mM; and (e) water.

2. The formulation according to claim 1, wherein said source of calcium ions is calcium chloride.

3. The formulation according to claim 1, wherein said plasma protein is a vitamin K-dependent plasma protein.

4. The formulation according to claim 3, wherein said vitamin K-dependent plasma protein is selected from the group consisting of Factor II, Factor VII, Factor IX, Factor X, Protein C, Protein S and Protein Z.

5. The formulation according to claim 1, wherein said plasma protein is a non-vitamin K-dependent plasma protein.

6. The formulation according to claim 5, wherein said non-vitamin K-dependent plasma protein is selected from the group consisting of Factor VIII and von Willebrand Factor.

7. A stable non-aqueous liquid formulation of a plasma protein comprising: (a) a plasma protein; and (b) a non-aqueous liquid, wherein said stable formulation contains substantially no water.

8. The formulation according to claim 7, wherein said non-aqueous liquid is selected from the group consisting of glycerol, dimethyl sulfoxide (DMSO), ethylene glycol, diethylene glycol, triethylene glycol, PEG 200, PEG 300, PEG 400, dipropylene glycol, tripropylene glycol, PPG 425, PPG 725, PPG 1000, PPG 2000, PPG 3000 and PPG 4000.

9. The formulation according to claim 7, wherein said plasma protein is a vitamin K-dependent plasma protein.

10. The formulation according to claim 9, wherein said vitamin K-dependent plasma protein is selected from the group consisting of Factor II, Factor VII, Factor IX, Factor X, Protein C, Protein S and Protein Z.

11. The formulation according to claim 7, wherein said plasma protein is a non-vitamin K-dependent plasma protein.

12. The formulation according to claim 11, wherein said non-vitamin K-dependent plasma protein is selected from the group consisting of Factor VIII and von Willebrand Factor.

13. A stable mixed aqueous/non-aqueous liquid formulation of a plasma protein comprising: (a) a plasma protein; (b) a non-aqueous liquid; and (c) water wherein said non-aqueous liquid in (b) is selected from the group consisting of: glycerol, dimethyl sulfoxide (DMSO), ethylene glycol diethylene glycol, triethylene glycol, PEG 200, PEG 300, PEG 400, dipropylene glycol, tripropylene glycol, PPG 425, PPG 725, PPG 1000. PPG 2000, PPG 3000 and PPG 4000.

14. A stable aqueous liquid formulation of a plasma protein comprising: (a) a plasma protein; (b) a pH buffering compound; (c) calcium chloride in a concentration of 0.1–40 mM; (d) an osmotic modulating agent; and (e) water.

15. A stable aqueous liquid formulation of a plasma protein comprising: (a) a plasma protein; (b) a pH buffering compound in a concentration of 0.1–100 mM; (c) a source of calcium ions; (d) an osmotic modulating agent; and (e) water.

16. The formulation according to claim 14 or 15, wherein said plasma protein is a vitamin K-dependent plasma protein.

17. The formulation according to claim 16, wherein said vitamin K-dependent plasma protein is selected from the group consisting of Factor II, Factor VII, Factor IX, Factor X, Protein C, Protein S and Protein Z.

18. The formulation according to claim 14 or 15, wherein said plasma protein is a non-vitamin K-dependent plasma protein.

19. The formulation according to claim 18, wherein said non-vitamin K-dependent plasma protein is selected from the group consisting of Factor VIII and von Willebrand Factor.

20. A stable aqueous liquid formulation of a plasma protein prepared by mixing together ingredients comprising (a) a plasma protein; (b) a pH buffering compound; (c) a source of calcium ions; (d) an osmotic modulating agent in a concentration of 1–500 mM; and (e) water.

21. A stable aqueous liquid formulation of a plasma protein prepared by mixing together ingredients comprising (a) a plasma protein; (b) a pH buffering compound; (c) calcium chloride in a concentration of 0.1–40 mM; (d) an osmotic modulating agent; and (e) water.

22. A stable aqueous liquid formulation of a plasma protein prepared by mixing together ingredients comprising (a) a plasma protein; (b) a pH buffering compound in a concentration of 0.1–100 mM; (c) a source of calcium ions; (d) an osmotic modulating agent; and (e) water.

* * * * *